(12) United States Patent
Hibner

(10) Patent No.: US 7,828,748 B2
(45) Date of Patent: Nov. 9, 2010

(54) VACUUM SYRINGE ASSISTED BIOPSY DEVICE

(75) Inventor: John A. Hibner, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 815 days.

(21) Appl. No.: 11/465,143

(22) Filed: Aug. 17, 2006

(65) Prior Publication Data

US 2007/0032743 A1 Feb. 8, 2007

Related U.S. Application Data

(63) Continuation-in-part of application No. 11/198,558, filed on Aug. 5, 2005.

(51) Int. Cl.
*A61B 10/00* (2006.01)
(52) U.S. Cl. .................................................. 600/568
(58) Field of Classification Search .......... 600/562–268
See application file for complete search history.

(56) References Cited

U.S. PATENT DOCUMENTS

| | | |
|---|---|---|
| 3,630,192 A | 12/1971 | Jamshidi |
| 4,051,852 A | 10/1977 | Villari |
| 4,600,014 A | 7/1986 | Beraha |
| 4,782,833 A | 11/1988 | Einhorn |
| 5,234,000 A | 8/1993 | Hakky et al. |
| 5,406,959 A | 4/1995 | Mann |
| 5,526,822 A | 6/1996 | Burbank et al. |
| 5,601,585 A | 2/1997 | Banik et al. |
| 5,645,209 A | 7/1997 | Green et al. |
| 5,649,547 A | 7/1997 | Ritchart et al. |
| 5,769,086 A | 6/1998 | Ritchart et al. |
| 5,775,333 A | 7/1998 | Burbank et al. |
| 5,876,329 A | 3/1999 | Harhen |

(Continued)

FOREIGN PATENT DOCUMENTS

EP    0 995 400    4/2000

(Continued)

OTHER PUBLICATIONS

U.S. Appl. No. 60/874,792, filed Dec. 13, 2006, Hibner, John A.

(Continued)

*Primary Examiner*—Max Hindenburg
*Assistant Examiner*—Brian Szmal
(74) *Attorney, Agent, or Firm*—Frost Brown Todd LLC

(57) ABSTRACT

A biopsy device and method are provided for obtaining a tissue sample, such as a breast tissue biopsy sample. The biopsy device includes a disposable probe assembly with an outer cannula having a distal piercing tip, a cutter lumen, and a cutter tube that rotates and translates past a side aperture in the outer cannula to sever a tissue sample. The biopsy device also includes a reusable handpiece with an integral motor and power source to make a convenient, untethered control for use with ultrasonic imaging. The reusable handpiece incorporates a probe oscillation mode to assist when inserting the distal piercing tip into tissue. The motor also actuates a vacuum syringe in coordination with movement of the cutter tube to provide vacuum assistance in prolapsing tissue and retracting tissue samples.

16 Claims, 21 Drawing Sheets

U.S. PATENT DOCUMENTS

| | | | |
|---|---|---|---|
| 5,928,164 A | 7/1999 | Burbank et al. | |
| 5,964,716 A | 10/1999 | Gregoire et al. | |
| 5,980,469 A | 11/1999 | Burbank et al. | |
| 6,007,497 A | 12/1999 | Huitema | |
| 6,017,316 A | 1/2000 | Ritchart et al. | |
| 6,077,230 A | 6/2000 | Gregoire et al. | |
| 6,083,177 A | 7/2000 | Kobren et al. | |
| 6,086,544 A | 7/2000 | Hibner et al. | |
| 6,120,462 A | 9/2000 | Hibner et al. | |
| 6,142,946 A | 11/2000 | Hwang et al. | |
| 6,213,957 B1 | 4/2001 | Milliman et al. | |
| 6,228,055 B1 | 5/2001 | Foerster et al. | |
| 6,231,522 B1 | 5/2001 | Voegele et al. | |
| 6,273,862 B1 | 8/2001 | Privitera et al. | |
| 6,428,486 B2 | 8/2002 | Ritchart et al. | |
| 6,485,436 B1 | 11/2002 | Truckai et al. | |
| 6,544,194 B1 | 4/2003 | Kortenbach et al. | |
| 6,620,111 B2 | 9/2003 | Stephens et al. | |
| 6,638,235 B2 | 10/2003 | Miller et al. | |
| 6,659,338 B1 | 12/2003 | Dittmann et al. | |
| 6,758,824 B1 | 7/2004 | Miller | |
| 6,849,080 B2 | 2/2005 | Lee et al. | |
| 7,025,098 B2 | 4/2006 | Osborne | |
| 7,226,424 B2 | 6/2007 | Ritchart et al. | |
| 2002/0082518 A1 | 6/2002 | Weiss et al. | |
| 2002/0120212 A1 | 8/2002 | Ritchart et al. | |
| 2003/0199753 A1 | 10/2003 | Hibner et al. | |
| 2004/0153003 A1 | 8/2004 | Cicenas et al. | |
| 2005/0049521 A1 | 3/2005 | Miller et al. | |
| 2005/0165328 A1 | 7/2005 | Heske et al. | |
| 2005/0215921 A1 | 9/2005 | Hibner et al. | |
| 2006/0041230 A1 | 2/2006 | Davis | |
| 2006/0074344 A1 | 4/2006 | Hibner | |
| 2006/0074345 A1 | 4/2006 | Hibner et al. | |
| 2006/0258955 A1 | 11/2006 | Hoffman et al. | |
| 2007/0032741 A1 | 2/2007 | Hibner et al. | |
| 2007/0032742 A1 | 2/2007 | Monson | |
| 2007/0213630 A1* | 9/2007 | Beckman et al. | 600/562 |
| 2007/0239067 A1 | 10/2007 | Hibner | |
| 2008/0004545 A1 | 1/2008 | Garrison | |

FOREIGN PATENT DOCUMENTS

| | | |
|---|---|---|
| EP | 1 520 518 | 4/2005 |
| EP | 1 832 234 | 12/2007 |
| EP | 1932482 | 6/2008 |
| WO | WO 03/077768 | 9/2003 |
| WO | WO 2004/052212 | 6/2004 |
| WO | WO 2006/124489 | 11/2006 |
| WO | WO 2007/019152 | 2/2007 |
| WO | WO 2007/021904 | 2/2007 |
| WO | WO 2007/112751 | 10/2007 |

OTHER PUBLICATIONS

U.S. Appl. No. 60/869,736, filed Dec. 13, 2006, Hibner, John A.
U.S. Appl. No. 11/782,893, filed Jul. 25, 2007, Garrison, William.
EnCor MRI Specifications and Breast Biopsy System, SenoRx, 2005, pp. 102.
ISR dated Jul. 18, 2007 for PCT Application No. PCT/US 06/30022.
ESR dated Dec. 20, 2007 for EPO Application No. 07253220.
Non-final Rejection dated Mar. 20, 2008 for U.S. Appl. No. 11/782,963.
Non-final Rejection dated Apr. 4, 2008 for U.S. Appl. No. 11/736,117.
Final Rejection dated Sep. 26, 2008 for U.S. Appl. No. 11/782,963.
Non Final Rejection dated Oct. 6, 2008 for U.S. Appl. No. 11/736,117.
International Search Report dated Sep. 27, 2007 for Application No. PCT/US06/30022.
International Search Report dated Dec. 18, 2008 for Application No. PCT/US2008/058627.
European Search Report dated Nov. 14, 2007 for Application No. 07250926.
European Search Report dated Apr. 3, 2009 for Application No. 08252518.
European Search Report dated Apr. 3, 2009 for Application No. 08252524.
European Examination Report dated Mar. 19, 2009 for Application No. 07250926.
Patentability Report and Written Opinion dated Feb. 5, 2008 for Application No. PCT/US2006/030022.
Supplemental European Search Report dated Dec. 16, 2009 for Application No. EP06789155.
European Communication dated Apr. 26, 2010 for Application No. 08252524.

* cited by examiner

VACUUM SYRINGE ASSISTED BIOPSY DEVICE

CROSS REFERENCE TO RELATED APPLICATIONS

The present application is a continuation-in-part of the co-pending and commonly-owned U.S. patent application Ser. No. 11/198,558, "BIOPSY DEVICE WITH REPLACEABLE PROBE AND INCORPORATING VIBRATION INSERTION ASSIST AND STATIC VACUUM SOURCE SAMPLE STACKING RETRIEVAL" to Hibner et al., filed 5 Aug. 2005, the disclosure of which is hereby incorporated by reference in its entirety.

FIELD OF THE INVENTION

The present invention relates in general to biopsy devices, and more particularly to biopsy devices having a cutter for severing tissue, and even more particularly to biopsy devices for multiple sampling with a probe remaining inserted.

BACKGROUND OF THE INVENTION

When a suspicious tissue mass is discovered in a patient's breast through examination, ultrasound, MRI, X-ray imaging or the like, it is often necessary to perform a biopsy procedure to remove one or more samples of that tissue in order to determine whether the mass contains cancerous cells. A biopsy may be performed using an open or percutaneous method.

An open biopsy is performed by making a large incision in the breast and removing either the entire mass, called an excisional biopsy, or a substantial portion of it, known as an incisional biopsy. An open biopsy is a surgical procedure that is usually done as an outpatient procedure in a hospital or a surgical center, involving both high cost and a high level of trauma to the patient. Open biopsy carries a relatively higher risk of infection and bleeding than does percutaneous biopsy, and the disfigurement that sometimes results from an open biopsy may make it difficult to read future mammograms. Further, the aesthetic considerations of the patient make open biopsy even less appealing due to the risk of disfigurement. Given that a high percentage of biopsies show that the suspicious tissue mass is not cancerous, the downsides of the open biopsy procedure render this method inappropriate in many cases.

Percutaneous biopsy, to the contrary, is much less invasive than open biopsy. Percutaneous biopsy may be performed using fine needle aspiration (FNA) or core needle biopsy. In FNA, a very thin needle is used to withdraw fluid and cells from the suspicious tissue mass. This method has an advantage in that it is very low-pain, so low-pain that local anesthetic is not always used because the application of it may be more painful than the FNA itself. However, a shortcoming of FNA is that only a small number of cells are obtained through the procedure, rendering it relatively less useful in analyzing the suspicious tissue and making an assessment of the progression of the cancer less simple if the sample is found to be malignant.

During a core needle biopsy, a small tissue sample is removed allowing for a pathological assessment of the tissue, including an assessment of the progression of any cancerous cells that are found. The following patent documents disclose various core biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; and US Patent Application 2003/0199753 published Oct. 23, 2003 to Hibner et al.

At present, a biopsy instrument marketed under the trade name MAMMOTOME is commercially available from ETHICON ENDO-SURGERY, INC. for use in obtaining breast biopsy samples. This device generally retrieves multiple core biopsy samples from one insertion into breast tissue with vacuum assistance. In particular, a cutter tube is extended into a probe to cut tissue prolapsed into a side aperture under vacuum assistance and then the cutter tube is fully retracted between cuts to extract the sample.

With a long probe, the rate of sample taking is limited not only by the time required to rotate or reposition the probe but also by the time needed to translate the cutter. As an alternative to this "long stroke" biopsy device, a "short stroke" biopsy device is described in the following commonly assigned patent applications: U.S. patent application Ser. No. 10/676,944, "Biopsy Instrument with Internal Specimen Collection Mechanism" filed Sep. 30, 2003 in the name of Hibner et al.; and U.S. patent application Ser. No. 10/732,843, "Biopsy Device with Sample Tube" filed Dec. 10, 2003 in the name of Cicenas et al. The cutter is cycled across the side aperture, reducing the sample time. Several alternative specimen collection mechanisms are described that draw samples through the cutter tube, all of which allow for taking multiple samples without removing the probe from the breast.

The vacuum assistance presented at the side aperture provides a further benefit of reducing the accumulation of bodily fluids around the probe that may tend to interfere with taking a diagnostic image, may impede subsequent insufflation and marker deployment, leave an undesirable hematoma at the biopsy site, and/or result in external bleeding that is a biohazard and may increase the patient's discomfort.

While the vacuum assistance has a number of benefits, some practitioners prefer to perform core biopsy procedures with simpler devices that do not include a control module with graphical user interface, electronic control, vacuum generation and control, and other features. In addition to the desire to reduce capital costs, it is also generally desirable to reduce the need to tether a hand-held biopsy device to sources of mechanical motion, vacuum supply, electrical power and control. Such tethers may tend to impede positioning of the biopsy device, introduce tripping hazards, and increase set up time.

Therefore, while these multiple sample core biopsy instruments have numerous advantages, it is believed that the diagnostic and therapeutic advantages of the core biopsy procedures would be seen as more desirable if vacuum assistance could be incorporated in a more convenient manner.

SUMMARY OF THE INVENTION

The present invention addresses these and other problems of the prior art by providing a biopsy device that has a probe cannula that is inserted into tissue to obtain a core biopsy sample by translating a cutter with the probe cannula. Vacuum assistance to prolapse tissue for sampling is advantageously provided by an integral vacuum container whose internal pressure is reduced from atmospheric pressure by actuation of a single motor that also translates the cutter to sever biopsy samples.

In one aspect of the invention, a biopsy device handpiece has a motorized translation drive mechanism that engages and operates a disposable probe assembly that also translates a vacuum plunger of a vacuum syringe. A cutter tube translating within a cutter lumen severs tissue that is prolapsed therein under the urging from vacuum supplied by the vacuum syringe.

These and other objects and advantages of the present invention shall be made apparent from the accompanying drawings and the description thereof.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

DETAILED DESCRIPTION OF THE INVENTION

Figure 1:
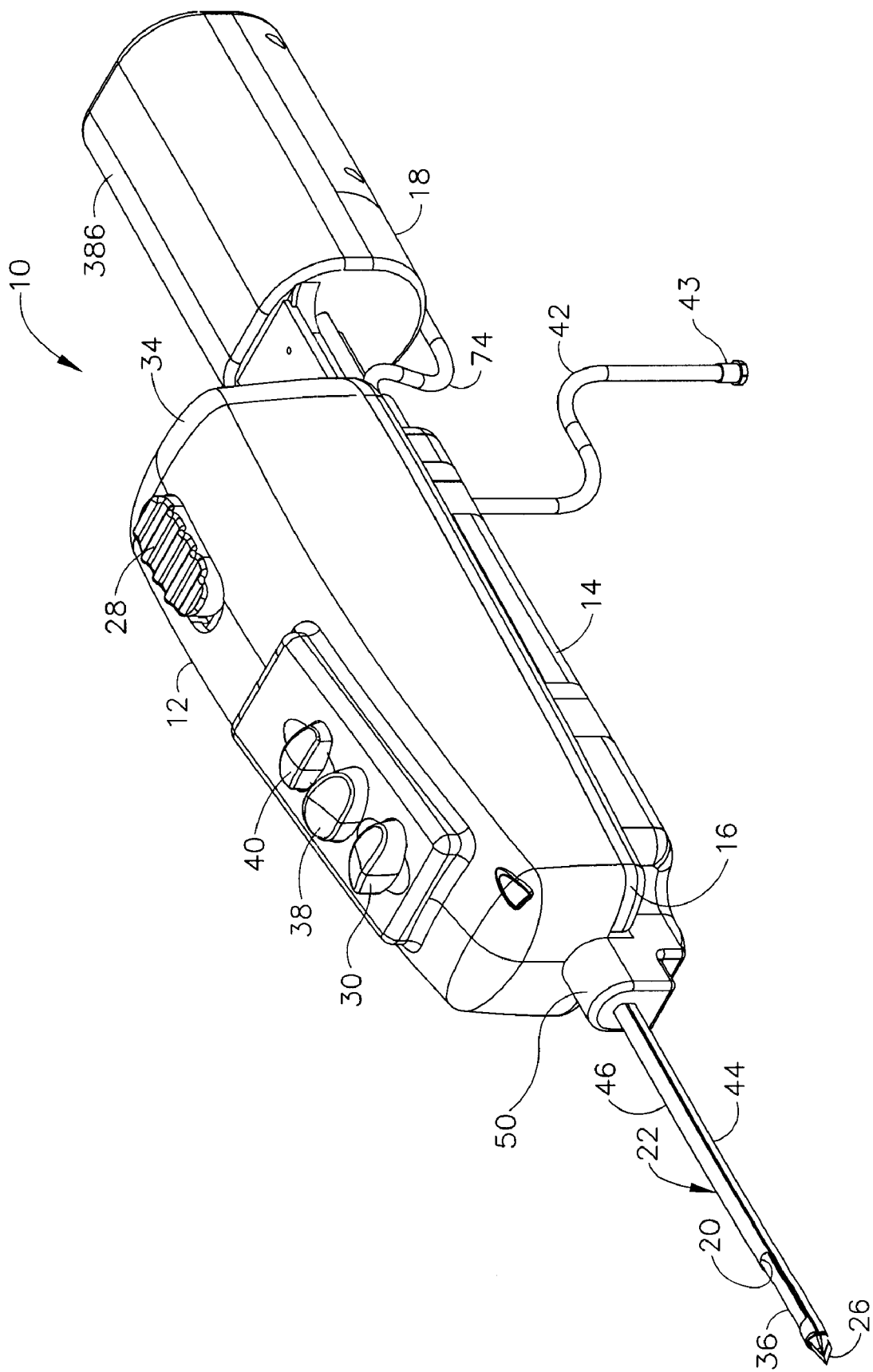
FIG. 1 is an isometric view of a biopsy device with attached vacuum syringe assembly consistent with the present invention.
Figure 2:
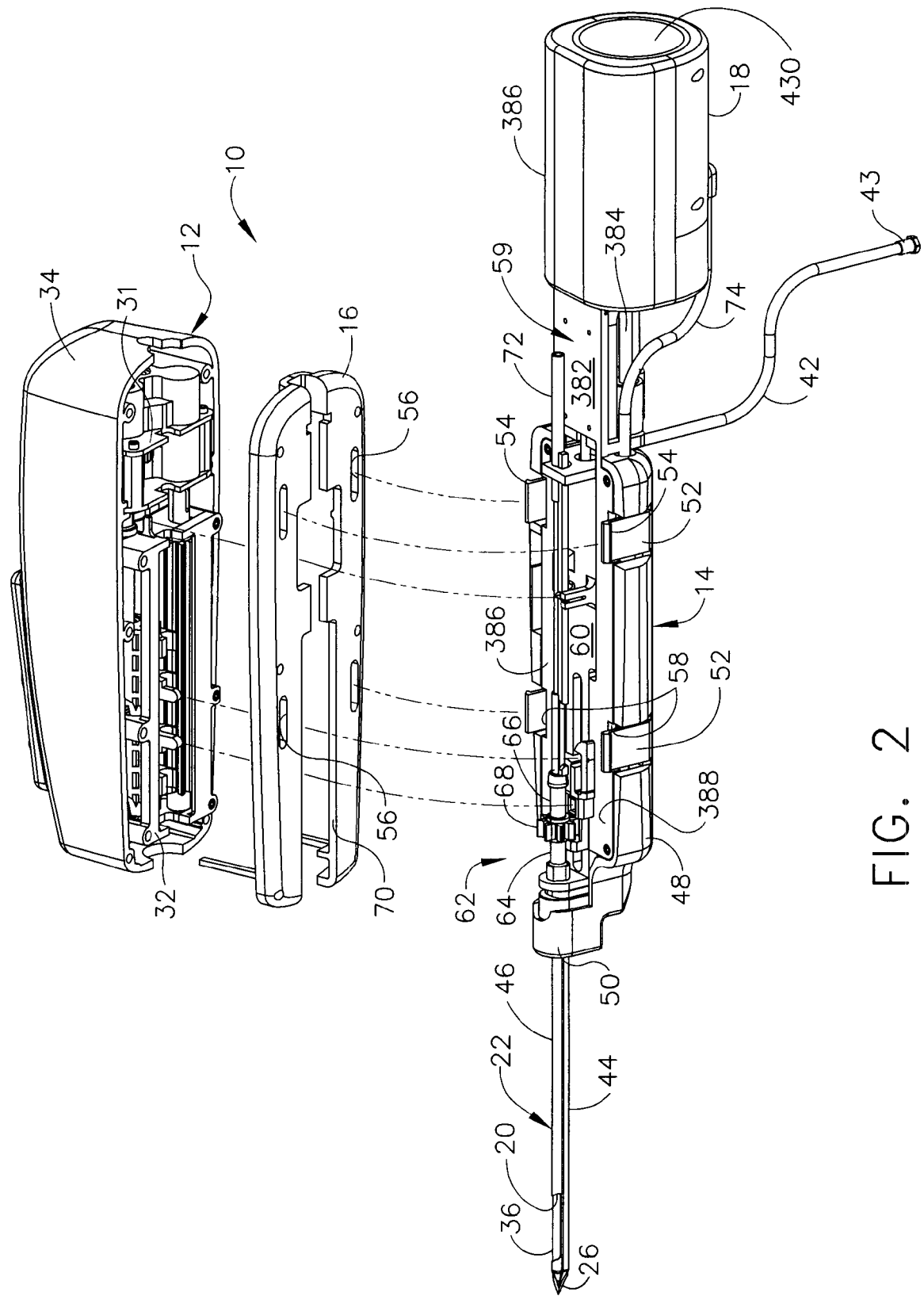
FIG. 2 is an isometric view of the biopsy device of FIG. 1 with a disposable probe assembly that includes the vacuum syringe assembly disengaged from a reusable handpiece that has a lower tray removed to expose a carriage frame assembly and a motor drive assembly.
Figure 3:
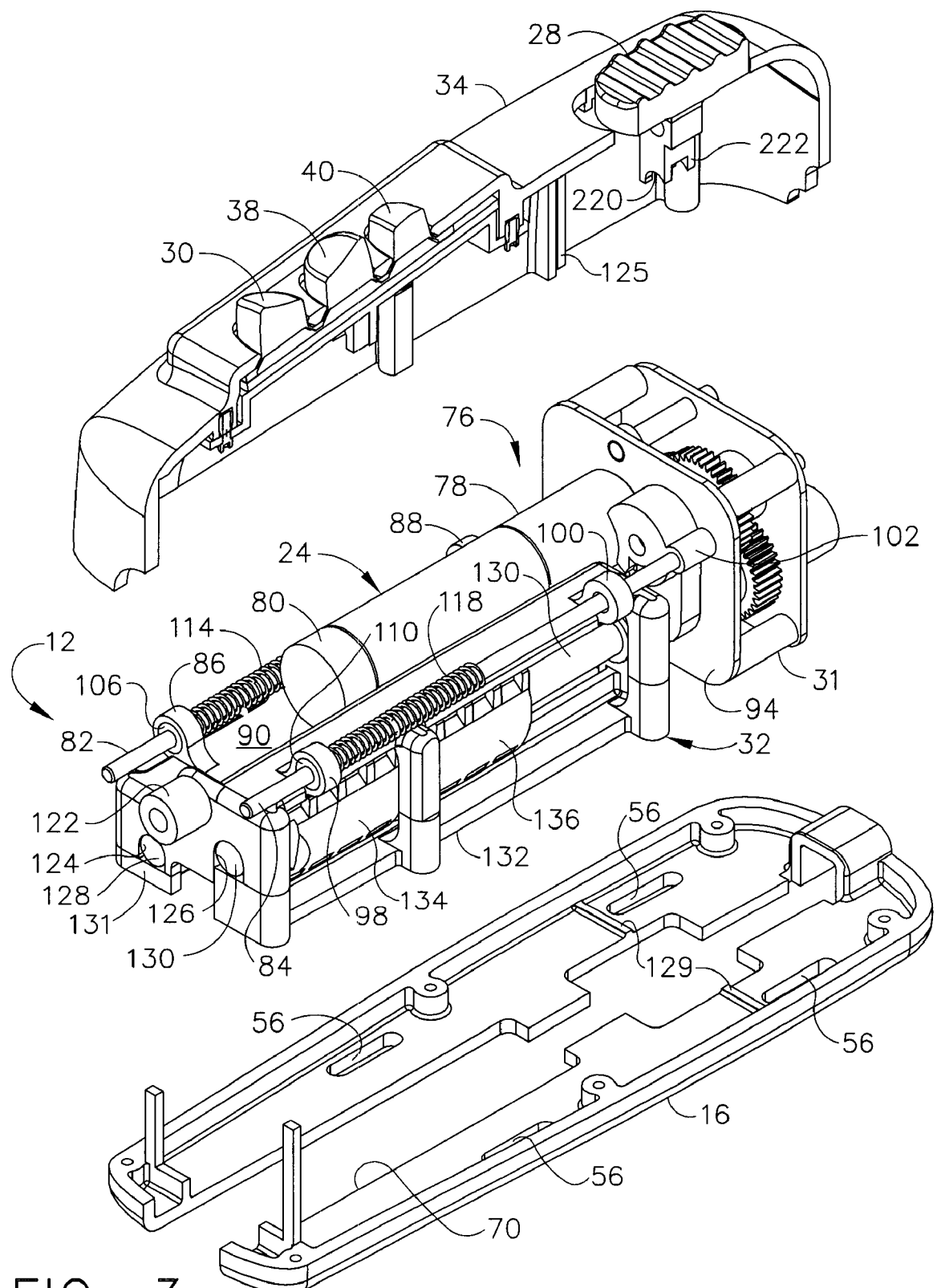
FIG. 3 is an isometric view of the reusable handpiece of FIG. 1 with a top cover detached with a left half cut away and with the lower handle tray detached to expose the motor drive assembly operatively engaged to the carriage frame assembly.

Turning to the Drawings, wherein like numerals denote like components throughout the several views, in FIGS. 1-3, a biopsy device 10 includes a reusable handpiece 12, and a disposable probe assembly 14. A lower handle tray 16 is disassembled from upper portions of the reusable handpiece 12 to expose portions that operably engage the disposable probe assembly 14. A vacuum syringe assembly 18 is a proximal portion of the disposable probe assembly 14 that is also actuated by the reusable handpiece 12. With the close proximity of the source of vacuum, the amount of vacuum line that needs to be evacuated is minimized, enabling a modestly sized vacuum syringe assembly 18 to effect vacuum assistance to prolapse tissue into a side aperture 20 of a probe cannula 22 of the disposable probe assembly 14. In FIG. 3, further economy is realized by employing one DC motor 24 in the reusable handpiece 12 to accomplish the severing of tissue samples as well as actuating the vacuum syringe assembly 18.

Figures 13, 14:
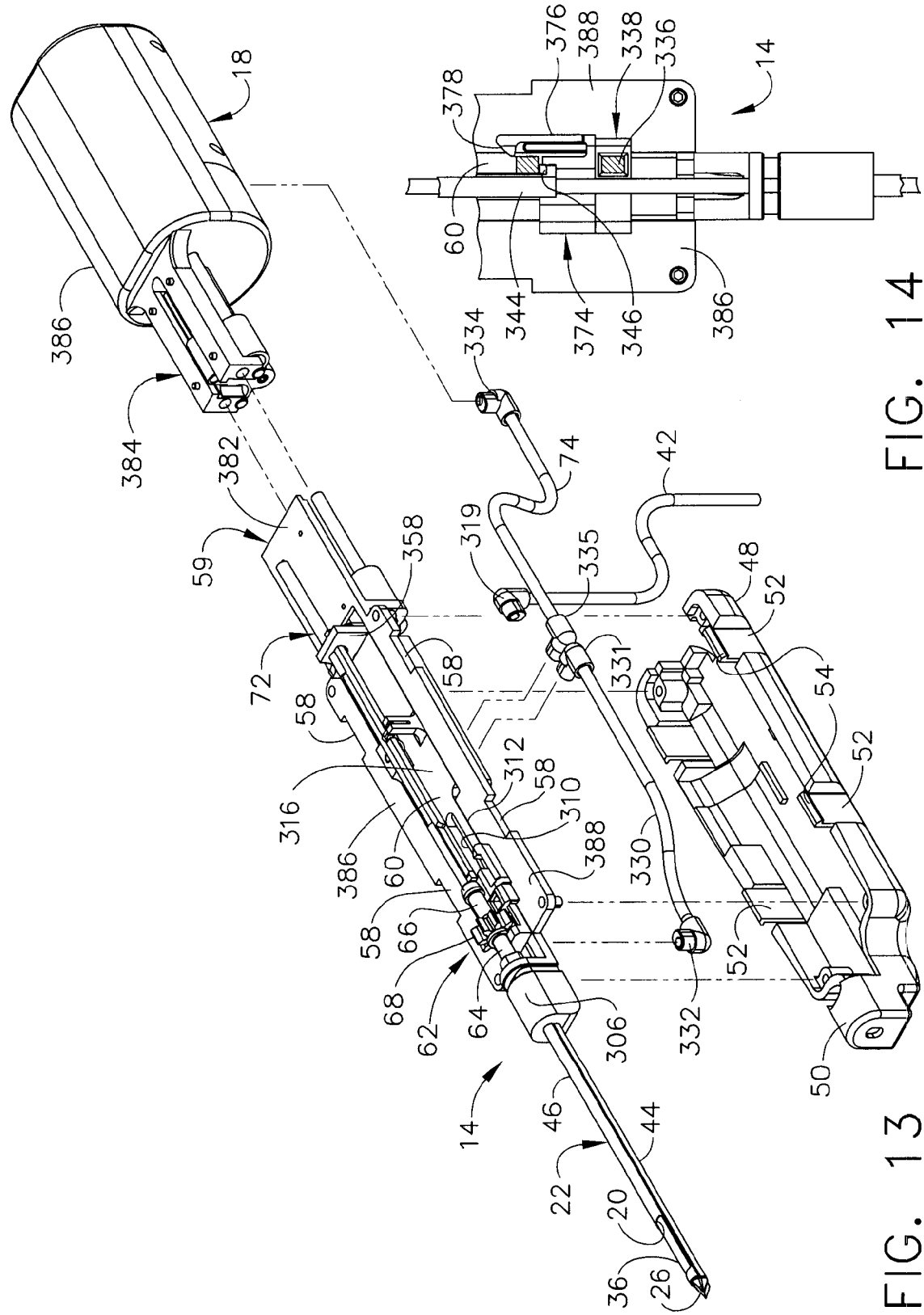
FIG. 13 is a front left isometric view of the disposable probe assembly of FIG. 1 with a bottom cover, vacuum conduits and vacuum syringe assembly disassembled.
FIG. 14 is a top detail view of a cutter gear and surrounding components of the disposable probe assembly of FIG. 1.

With particular reference to FIG. 1, insertion of the probe cannula 22 into tissue is integrally supported by a piercing tip 26 attached at a distal end as well as a longitudinal jack hammer motion to the probe cannula 22 selected by positioning a slide button 28 distally and depressing a forward motor button 30. In response, the DC motor 24 drives a transmission section 31 grounded to a top cover 34 of the reusable handpiece 12 to longitudinally reciprocate an internal carriage frame assembly 32 that is engaged for movement with the probe cannula 22 (FIG. 3). With the slide button 28 proximally positioned, depression of the forward motor button 30 causes the DC motor 24 to advance and rotate a cutter tube 36, depicted in FIG. 1 as having been fully distally translated, closing the side aperture 20. Depression of a reverse motor button 38 causes the cutter tube 36 to retract. Depression of a mode button 40 may cause other functions to be performed. For example, fluid may be applied to or removed from the biopsy device 10 via a valve (not shown), activated by mode button 40, inserted along distal vacuum conduit 330 (FIG. 13). An external conduit 42 extends from the disposable probe assembly 14, terminated by a filter/tube fitting 43. Vacuum assistance passes through a lateral lumen 44 of the probe cannula 22 and distally enters a cutter lumen 46 that encompasses the cutter tube 36 and includes the side aperture 20. It should be appreciated that the biopsy device 10 includes a minimum of "tethers" that would impede use, pose a tripping hazard, or extend set-up time.

Alternatively, instead of "hard-walled" lateral lumen 44 separated from the cutter lumen 46 along its length, applications consistent with the present invention may have a cylindrical probe cannula (not shown) wherein the cutter tube 36 is positioned off-center to translate across a side aperture. A "soft-walled" lateral lumen may then be defined as a space between an outer diameter of the cutter tube and an inner diameter of the cylindrical probe cannula.

In FIG. 2, the disposable probe assembly 14 has a bottom cover 48 with a distal probe mount cover 50 that assists in supporting the probe cannula 22 while allowing the longitudinal jack hammer motion. A plurality of locking tabs 52 with locking edges 54 extend upwardly through pass through slots 56 formed in the periphery of the lower handle tray 16 to resiliently extend outwardly into engaging contact with the slots 56. Relieved areas 58 formed behind each locking tab 52 in a top extension member 59 that surrounds a probe support body 60, the combination covering a cavity defined by the bottom cover 48, allow depression of the locking tabs 52 to unlock the disposable probe assembly 14 to install another identical or similar assembly.

A proximal end of the cutter tube 36 receives a cutter gear 62 having distal and proximal reduced diameter bearing surfaces 64, 66 on each longitudinal side of a rotation spur gear section 68, which engage the reusable handpiece 12 for rotation and for longitudinal translation through a distally open longitudinal aperture 70 formed in the lower handle tray 16. A straw assembly 72 is also engaged by the reusable handpiece 12 through the longitudinal aperture 70 to reciprocate longitudinally into a proximal opening of the cutter tube 36 and cutter gear 62 to encompass and retract tissue samples. A vacuum source conduit 74 communicates between the vacuum syringe assembly 18 and the bottom cover 48 of the disposable probe assembly 14.

Figure 4:
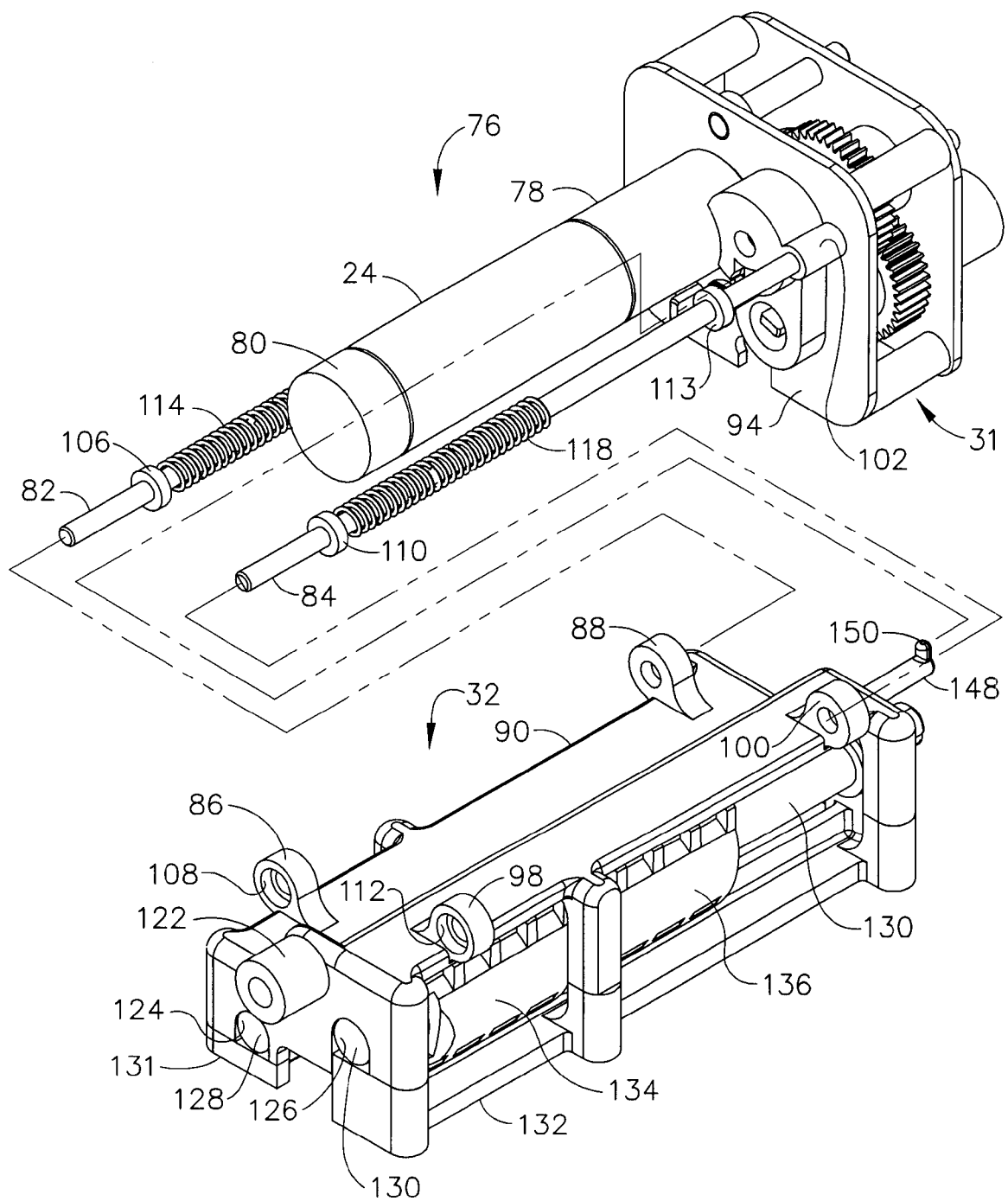
FIG. 4 is an isometric view of the motor drive assembly removed from the carriage frame assembly of FIG. 3.

In FIG. 3-13, the reusable handpiece 12 is depicted in various states of disassembly to illustrate its operation. The transmission section 31 is part of a rigidly mounted motor drive assembly 76 that includes the motor 24 in between a planetary gearbox 78 and an encoder 80. Battery or other power sources and control circuitry are omitted in the depictions. The motor drive assembly also includes a right guide pin 82 and a left guide pin 84. The motor drive assembly 76 is shown operably engaged to the longitudinally reciprocating carriage frame assembly 32 in FIG. 3 and disassembled from the longitudinally reciprocating carriage frame assembly in FIG. 4. In FIG. 4, the right guide pin 82 is inserted proximally through a right front pin guide 86 and then through a right rear pin guide 88 both part of an upper frame 90 of the carriage frame assembly 32. A proximal end of the right guide pin 82 resides within a distally projecting right pin receptacle 92 (FIG. 12) formed as part of a distal bulkhead 94 of the transmission section 31. A distal end of the right guide pin 82 is received by a right pin recess 96 (FIG. 5) formed in the top cover 34. Similarly, the left guide pin 84 is inserted proximally through a left front pin guide 98 and then through a left rear pin guide 100, both part of the upper frame 90 of the carriage frame assembly 32. A proximal end of the left guide pin 84 resides within a distally projecting left pin receptacle 102 respectively formed as part of the distal bulkhead 94 of the transmission section 31. A distal end of the left guide pin 84 is received by a left pin recess 104 (FIG. 5) formed in the top cover 34.

With particular reference to FIGS. 3, 4, 6, 7 and 12, a right front ring bearing 106 is inserted over a distal portion of the right guide pin 82 and is received within a cylindrical recess 108 formed on a distal side of the right front pin guide 86. A right aft ring bearing 109 is inserted over a proximal portion of the right guide pin 82 and is received within a cylindrical recess 111 (FIG. 6) formed on a proximal side of the right aft pin guide 88. A left front ring bearing 110 is inserted over a distal portion of the left guide pin 84 and is received within a cylindrical recess 112 formed on a distal side of the left front pin guide 98. A left aft ring bearing 113 (FIG. 9) is inserted over a proximal portion of the left guide pin 84 and is received within a cylindrical recess 115 (FIG. 6) formed on a proximal side of the left aft pin guide 100. A right compression spring 114 is proximally received over the right guide pin 82 between the right front and rear pin guides 86, 88. More particularly, the right compression spring 114 is distally positioned against the right front pin guide 86 and at its proximal end by a right downwardly projecting structure 116 (FIG. 5) formed on an interior of the top cover 34 that closely encompasses a top portion of the right guide pin 82 without contacting other portions of the carriage frame assembly 32. A left compression spring 118 is proximally received over the left guide pin 84 between the left front and rear pin guides 98, 100. More particularly, the left compression spring 118 is distally positioned against the left front pin guide 98 at its distal end by a left downwardly projecting structure 120 (FIG. 5) formed on the interior of the top cover 34 that closely encompasses a top portion of the left guide pin 84 without contacting other portions of the carriage frame assembly 32. Thereby, the carriage frame assembly 32 is biased to a distal position relative to the top cover 34 and lower handle tray 16.

Figure 5:
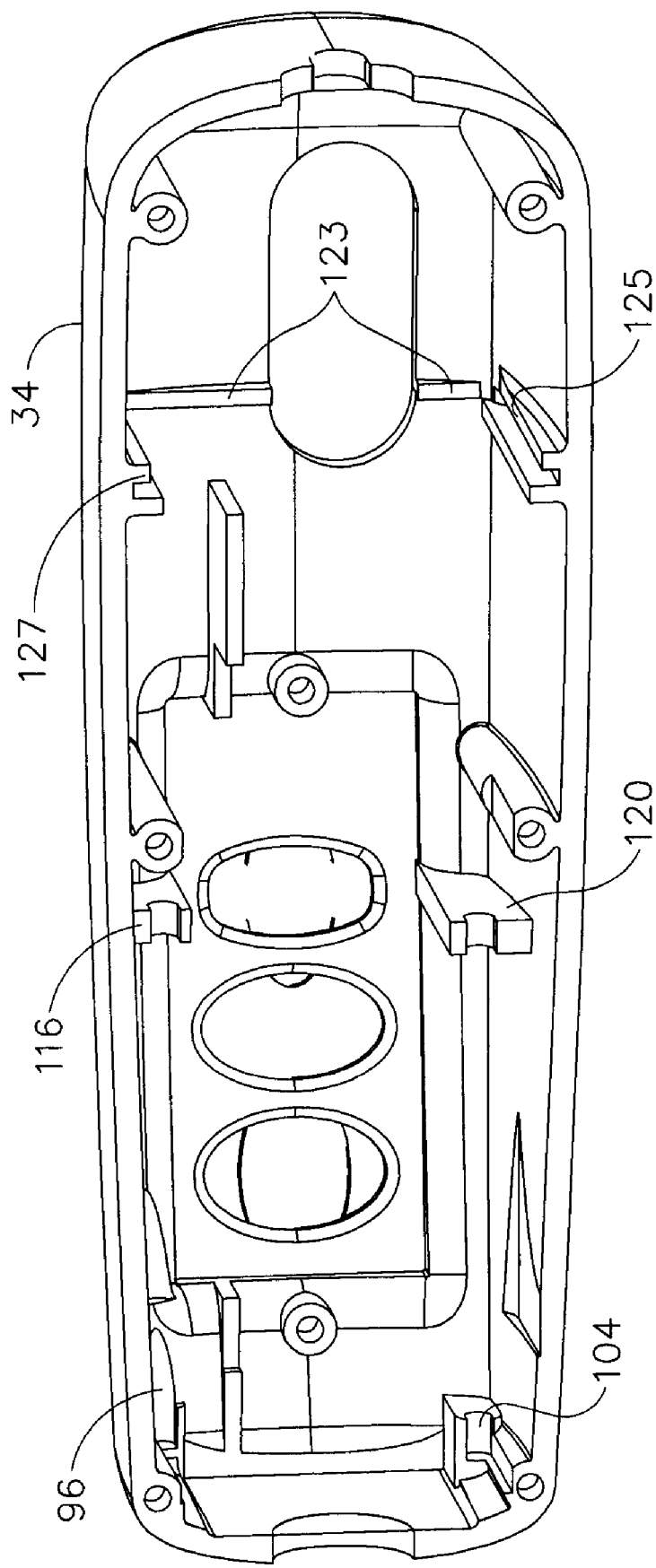
FIG. 5 is a bottom isometric view of the top cover of the reusable handpiece of FIG. 2.

In FIGS. 3-5, a forward projecting cylindrical resilient member 122 fastened to the upper frame 90 reduces noise by contacting the front interior of the top cover 34 slowing distal movement of the carriage frame assembly 32 prior to reaching full travel. The distal bulkhead 94 is restrained by being proximal to a top ridge 123, a right ridge 125, and a left ridge 127 (FIG. 5) formed in the interior of the top cover 34 and to a bottom ridge 129 formed on an upper surface of the lower handle tray 16.

Figure 6:
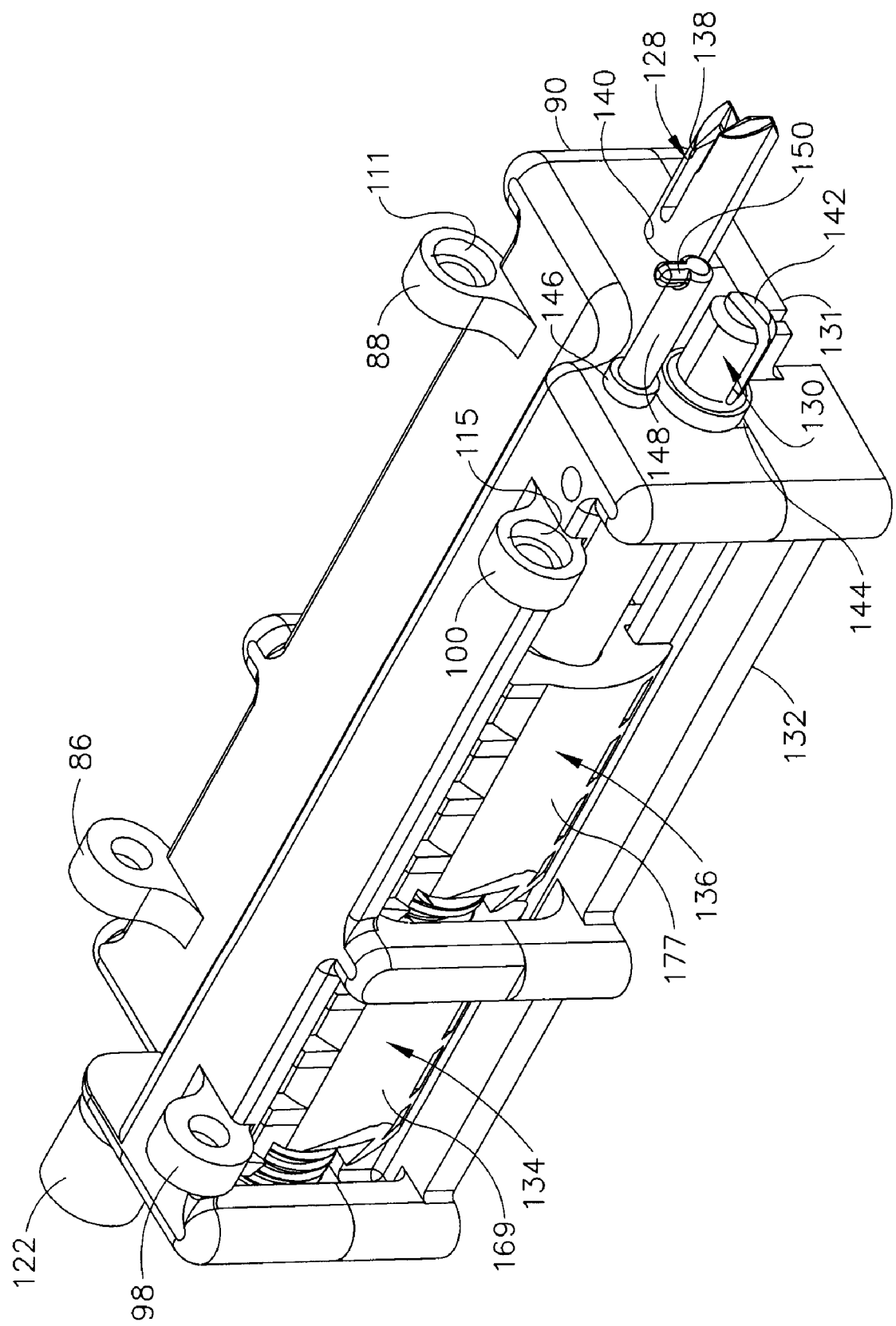
FIG. 6 is a top, left and aft isometric view of the carriage frame assembly of FIG. 4.
Figure 7:
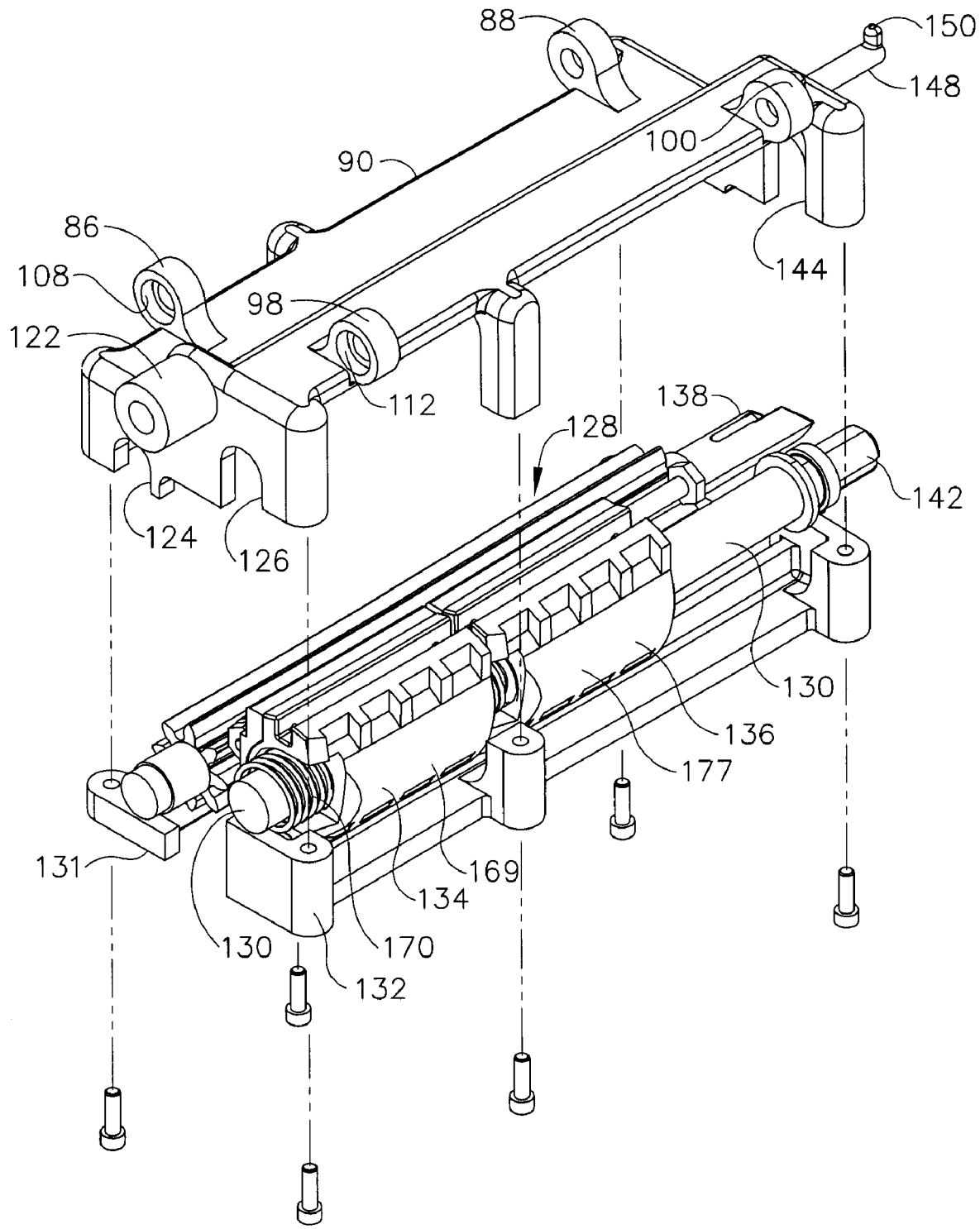
FIG. 7 is a top, left and forward view of the carriage frame assembly of FIG. 4 with an upper frame disassembled.

Returning to FIGS. 3-4 and 7, the upper frame 90 has right and left front shaft apertures 124, 126 that respectfully receive for rotation a distal end of a rotation shaft 128 and a translation shaft 130. The right front shaft aperture 124 is closed by the front portion of a right lower frame 131 of the carriage frame assembly 32. The left front shaft aperture 126 is closed by the front portion of a left lower frame 132 of the carriage frame assembly 32. A front (cutter) carriage 134 and an aft (straw) carriage 136 are received on the translation shaft 130 and are encompassed by the upper and lower frames 90, 132. In FIG. 6, a proximal beveled and slotted end 138 of the rotation shaft 128 extends out of right aft shaft aperture 140 formed in the upper frame 90 for engagement to the transmission section 31 and is closed by an aft portion of the lower frame 131. A proximal slotted end 142 of the translation shaft 130 extends out of a left aft aperture 144 formed in the upper frame 90 for engagement to the transmission section 31 and closed by the lower frame 132. A threaded receptacle 146 on the aft end of the upper frame 90 receives a proximally projecting bolt 148 having an upwardly directed strike pin 148 at its proximal end.

Figure 8:
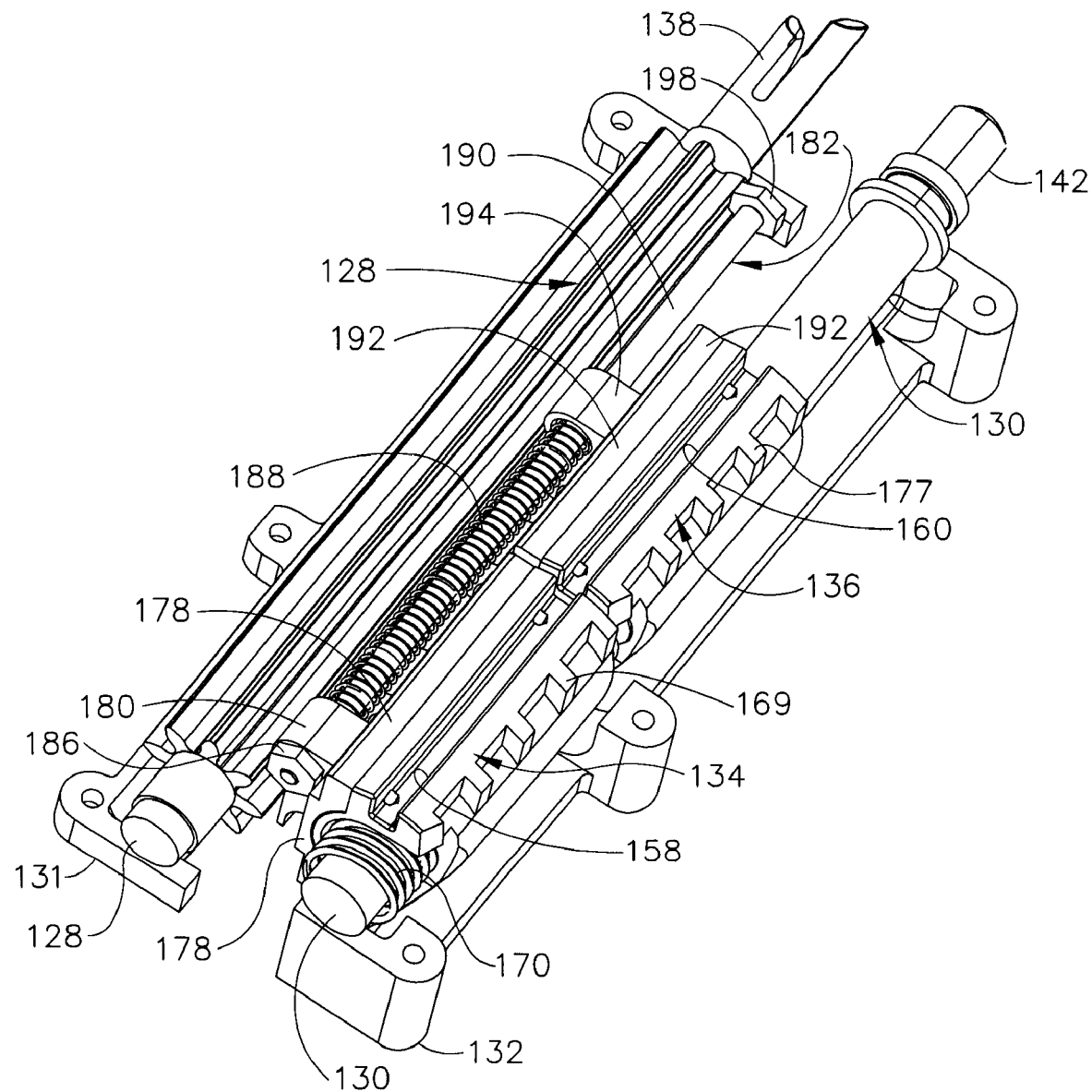
FIG. 8 is a top, left and front isometric view of the carriage frame assembly of FIG. 4 with the upper frame removed.
Figure 9:
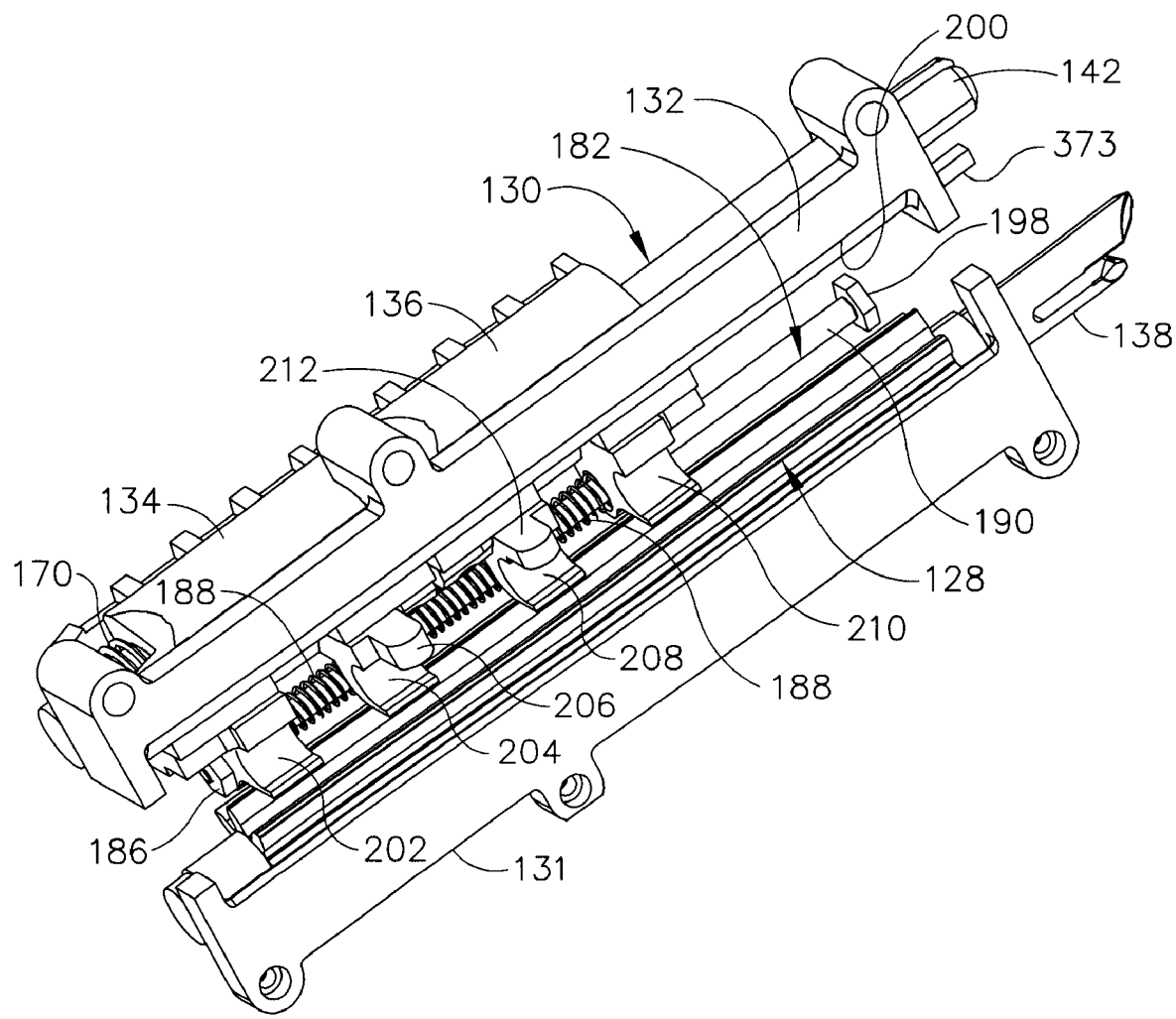
FIG. 9 is a bottom isometric view of the carriage frame assembly of FIG. 8 with the upper frame removed.
Figure 10:
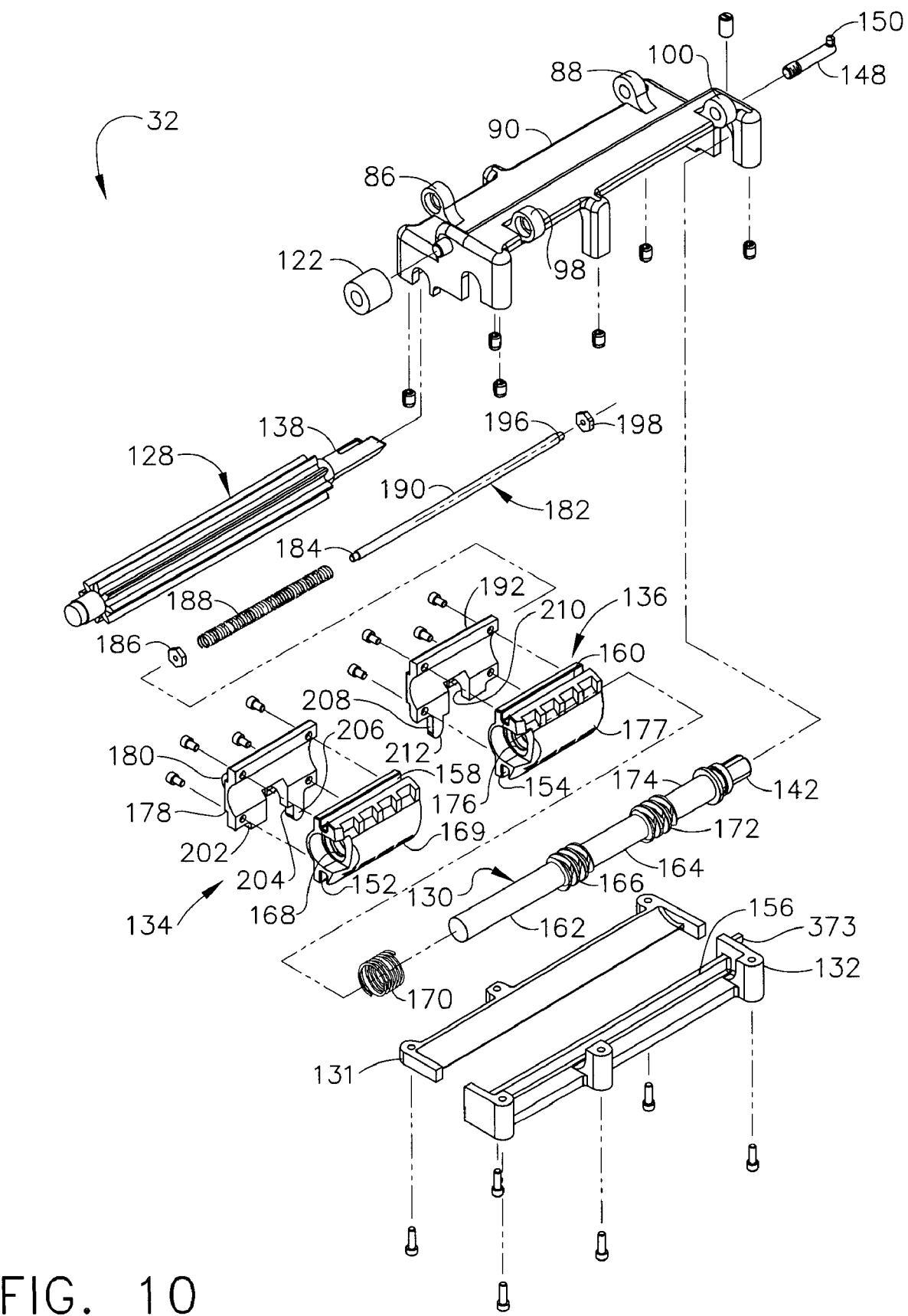
FIG. 10 is a top, left and front isometric exploded view of the carriage frame assembly of FIG. 4.

In FIGS. 7-10, the carriage frame assembly 32 sequences translation of the front and aft carriages 134, 136. With particular reference to FIG. 10, the front and aft carriages 134, 136 respectively include lower longitudinal grooves 152, 154 that slide upon a lower rail 156 upwardly presented on the left lower frame 132. The front and aft carriages 134, 136 respectively include an upper longitudinal groove 158, 160 that slides upon a rail (not shown) downwardly presented on the upper frame 90. The translation shaft 130 has a distal overrun portion 162 and a center overrun portion 164 separated by a front threaded portion 166 that a threaded bore 168 of a front main body portion 169 of the front carriage 134 traverses in response to rotation of the translation shaft 130. A front translation compression spring 170 on the translation shaft 130 distal to the front carriage 134 compresses to allow the front carriage 134 to free wheel when being distally advanced and then biases the front carriage 134 aft to engage the front threaded portion 166 for being retracted upon reversal of rotation of the translation shaft 130.

With particular reference to FIGS. 8 and 10, proximal to the center overrun portion 164 is an aft threaded portion 172 and then a proximal overrun portion 174 that a threaded bore 176 of a back main body portion 177 of the aft carriage 136 traverses in response to rotation of the translation shaft 130 as well as in response to a connection to the front carriage 134. In particular, a front bracket 178 mounted on a right side of the front carriage 134 has a rightward front pin guide 180 that receives a distal end of a longitudinally aligned carriage limiting rod 182. A distal threaded end 184 of the carriage limiting rod 182 extends distally out of the rightward front pin guide 180 and is prevented from backing out by a front nut 186. A long compression spring 188 is received over a shaft 190 of the carriage limiting rod 182 proximal to the rightward front pin guide 180. An aft bracket 192 is attached to a right side of the back main body portion 177 of the aft carriage 136 to extend a rightward aft pin guide 194 that receives the carriage limiting rod 182, which extends a proximal threaded end 196 proximally out of the rightward aft pin guide 194 to receive an aft nut 198 that limits forward movement. The long compression spring 188 biases the aft carriage 136 away from the front carriage 134, delaying retraction of a tissue sample until cutting is complete when full distal translation of the front carriage 134 pulls the aft carriage 136 onto the aft threaded portion 172.

With particular reference to FIG. 9, a lengthwise engagement aperture 200 defined between the right and left lower frames 131, 132 presents engaging structures that actuate the disposable probe assembly 14 and the vacuum syringe assembly 18. The rotation (spur) gear 128 exposes its left side to the lengthwise engagement aperture 200 for engagement with the rotation spur gear section 68 of the cutter gear 62 to impart a rotation. The front bracket 178 has a downward distal half cylinder recess 202 sized to grip the distal reduced diameter bearing surface 64 of the cutter gear 62 (FIG. 2). The front bracket 178 further has a downward proximal half cylinder recess 204 proximally spaced and sized to grip the proximal reduced diameter bearing surface 66 of the cutter gear 62 (FIG. 2) as well as a downwardly projecting front actuation finger 206 to the left side and below of the cutter gear 62 for selecting vacuum from the vacuum syringe assembly 18. Similarly, the aft bracket 192 has a downward distal half cylinder recess 208 and a downward proximal half cylinder recess 210 proximally spaced and sized to grip portions of the straw assembly 72 as applicable to effect retraction of tissue samples, as well as a downwardly projecting aft actuation finger 212 to the left side of the straw assembly 72.

Figure 11:
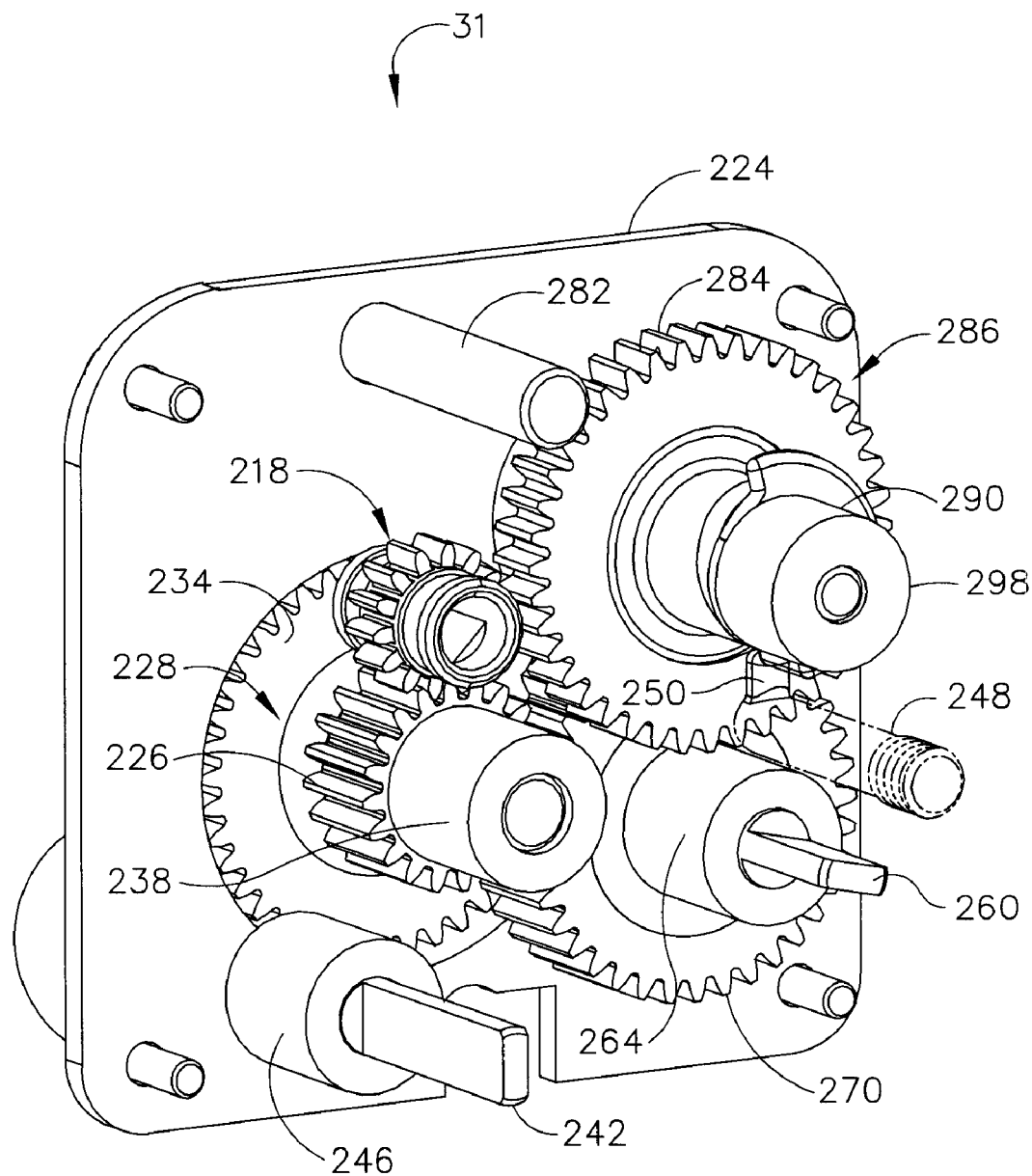
FIG. 11 is a right front view of a transmission section of the motor drive assembly of FIG. 4 with a distal bulkhead removed.
Figure 12:
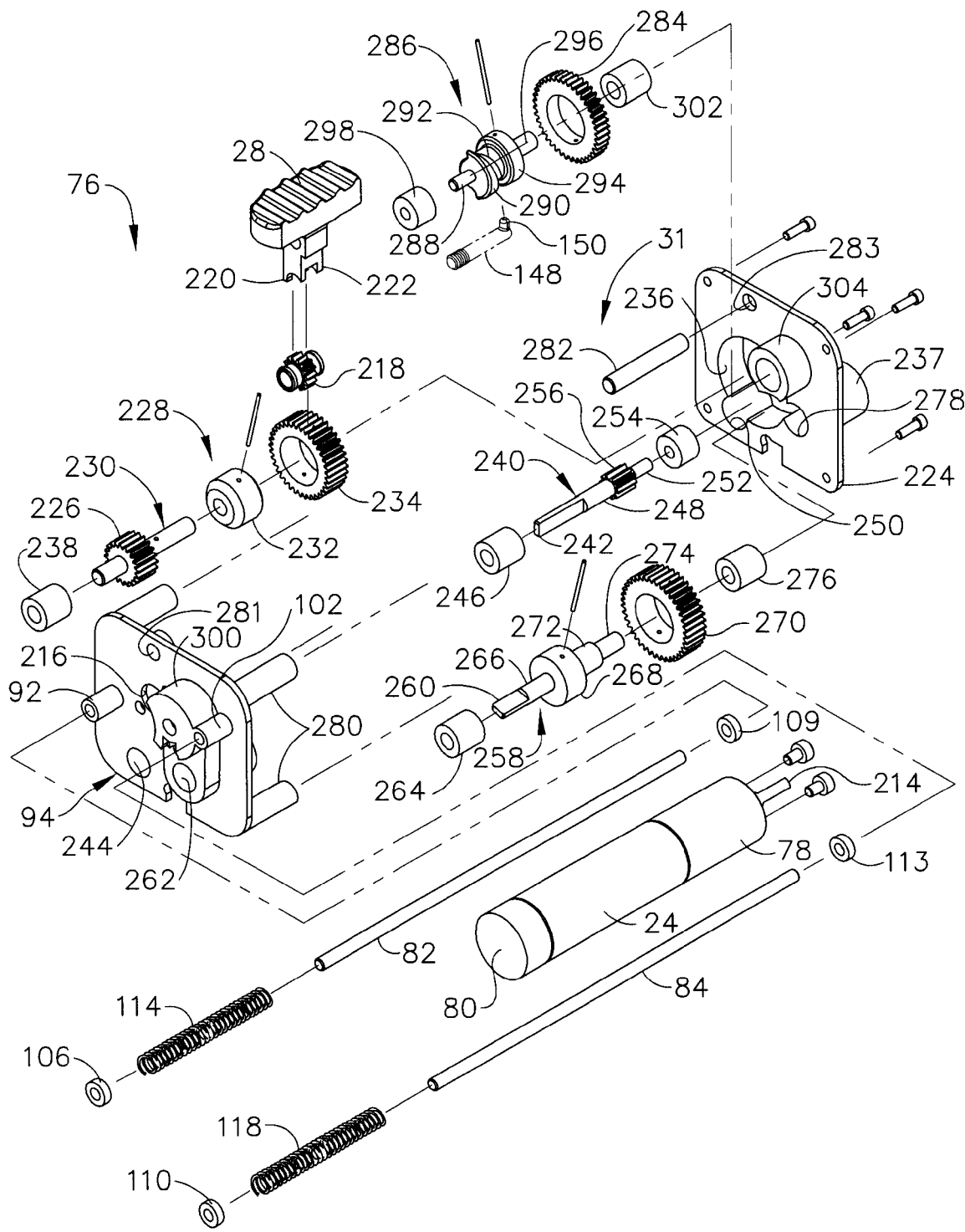
FIG. 12 is a front left exploded view of the transmission section of the motor drive assembly of FIG. 4.

In FIGS. 2-3 and 11-12, the motor drive assembly 76 rotates rotation and translation shafts 128, 130 at a fixed ratio to optimize cutting performance of the cutter tube 36 when the slide button 28 is back. Alternatively, the motor drive assembly 76 imparts a jackhammer vibration to the carriage frame assembly 32 when the slide button 28 is forward. With particular reference to FIGS. 11-12, the planetary gearbox 78 extends proximally a keyed motor drive shaft 214 (FIG. 12) through a drive shaft hole 216 formed in the distal bulkhead 94. A slide spur gear 218 is received upon the keyed motor drive shaft 214 remaining engaged for rotation between a first distal (jack hammer) position and a second proximal (translation) position in accordance with a position of the slide button 28 whose distal and proximal feet 220, 222 straddle the slide spur gear 218. In FIG. 11, the slide spur gear 218 is close to a proximal bulkhead 224 of the transmission section 31, engaging a small spur gear 226 of a multiplier gear assembly 228. The multiplier gear assembly 228 includes a longitudinal shaft 230 centrally attached to the small spur gear 226. Proximal thereto, a cylindrical hub 232 is pinned to the longitudinal shaft 230 and in turn is encompassed by and pinned to a large spur gear 234 that rotates within a correspondingly sized, distally open recess 236 formed in proximally projecting container 237 integral to the proximal bulkhead 224. A front cylinder bearing 238 received on a distal portion of the longitudinal shaft 230 is received by the proximal surface of the distal bulkhead 94.

A first output drive shaft 240 distally presents a right angle prismatic end 242 shaped to engage the beveled and slotted end 138 of the rotation shaft 128 that passes through a lower right hole 244 in the distal bulkhead 94. A cylindrical spacer 246 is received over a distal cylindrical portion 248 of the first output shaft 240, taking up the space between the rotation shaft 128 and the proximal bulkhead 224. A distally open recess 250, formed as part of the container 237 that communicates from below with the recess 236, is shaped to receive a proximal cylindrical end 252 of the first output drive shaft 240 and encompasses cylindrical bearing 254 as well as a small spur gear segment 256, which is distal thereto and engages the large spur gear 234 of the multiplier gear assembly 228.

A second output drive shaft 258 distally presents a right angle prismatic end 260 to engage the proximal slotted end 142 of the translation shaft 130 that extends through a low left hole 262 in the distal bulkhead 94. A cylindrical spacer 264 is received over a distal cylindrical portion 266 of the second output drive shaft 258 proximal to the right angle prismatic end 260 and distal to a wider diameter hub segment 268 that is encompassed by and pinned to a large spur gear 270 that engages the small spur gear 226 of the multiplier gear assembly 228. Proximal to the hub segment 268 is a wide spacer segment 272 and then a narrow cylindrical end 274 that receives a cylindrical bearing 276 that resides within a correspondingly-sized, distally open recess 278 that communicates from the left with the recess 236 and is formed as part of the same container 237.

The distal and proximal bulkheads 94, 224 are structurally attached to one another in parallel alignment traverse to the longitudinal axis of the biopsy device 10 by cylindrical legs 280 molded to and proximally projecting from rectangular corners of the distal bulkhead 94 and fastened to the proximal bulkhead 224. In addition, a pin 282 passes through holes 281, 283 longitudinally aligned in the distal and proximal bulkheads, 94, 224 respectively along a top surface.

When the slide button 28 is moved distally to the jackhammer position, the sliding spur gear 218 disengages from the small spur gear 226 and engages a large spur gear 284 of a rotary camming gear assembly 286. A camming shaft 286 from distal to proximal includes a distal cylindrical end 288, a cam wheel 290, a mid-shaft portion 292 that receives the upwardly directed strike pin 150 of the proximally projecting bolt 148, a wide diameter hub 294 that is encompassed by and pinned to the large spur gear 284, and a proximal cylindrical end 296. A distal cylindrical bearing 298 is received within a proximally open container 300 projecting distally from the distal bulkhead 94 and in turn receives the distal cylindrical end 288 of the camming shaft 286. A proximal cylindrical bearing 302 is received within a distally projecting and open cylinder 304 formed on the proximal bulkhead 224 and in turn receives the proximal cylindrical end 296 of the camming shaft 286.

As the camming shaft 286 rotates clockwise as viewed from behind, the cam wheel 290 presents a proximal surface to the distal edge of the strike pin 150 that is more proximal until the interrupted portion of the camming wheel 290 is presented, allowing the strike pin 150 to return to a distal position under the urging of the distal biasing of the right and left compression springs 114, 118.

In FIGS. 13-22, the disposable probe assembly 14 has movable components that respond to the actuating motions of the reusable handpiece 12. With particular reference to FIGS. 13-17, the probe support body 60 includes a distal probe mount 306 that is received within the distal probe mount cover 50 of the bottom cover 48. Proximal to and underlying a longitudinal axis of the disposable probe assembly 14 defined by a probe guide hole 308 passing through the distal probe mount 306, an upwardly open longitudinal trough 310 is formed into a necked portion 312 of the probe support body 60. At a proximal end of the longitudinal trough 310, an upper rod passage 314 longitudinally passes through an upper portion of a proximal block portion 316 of the probe support body 60. A distal vacuum pump rod 317 is received for longitudinal movement in the upper rod passage 314.

Figure 15:
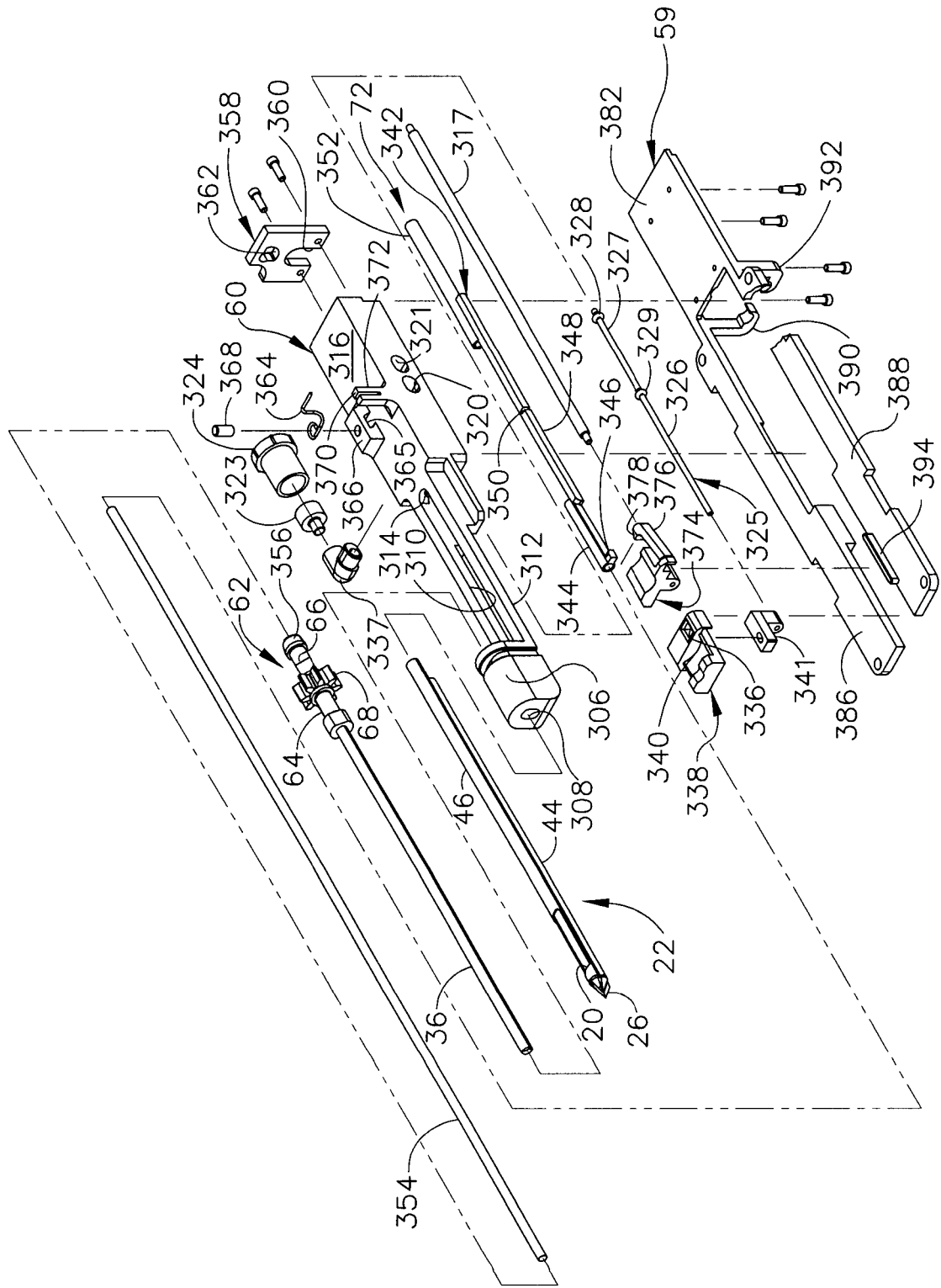
FIG. 15 is a left front exploded view of a distal portion of the disposable probe assembly of FIG. 1.
Figure 18:
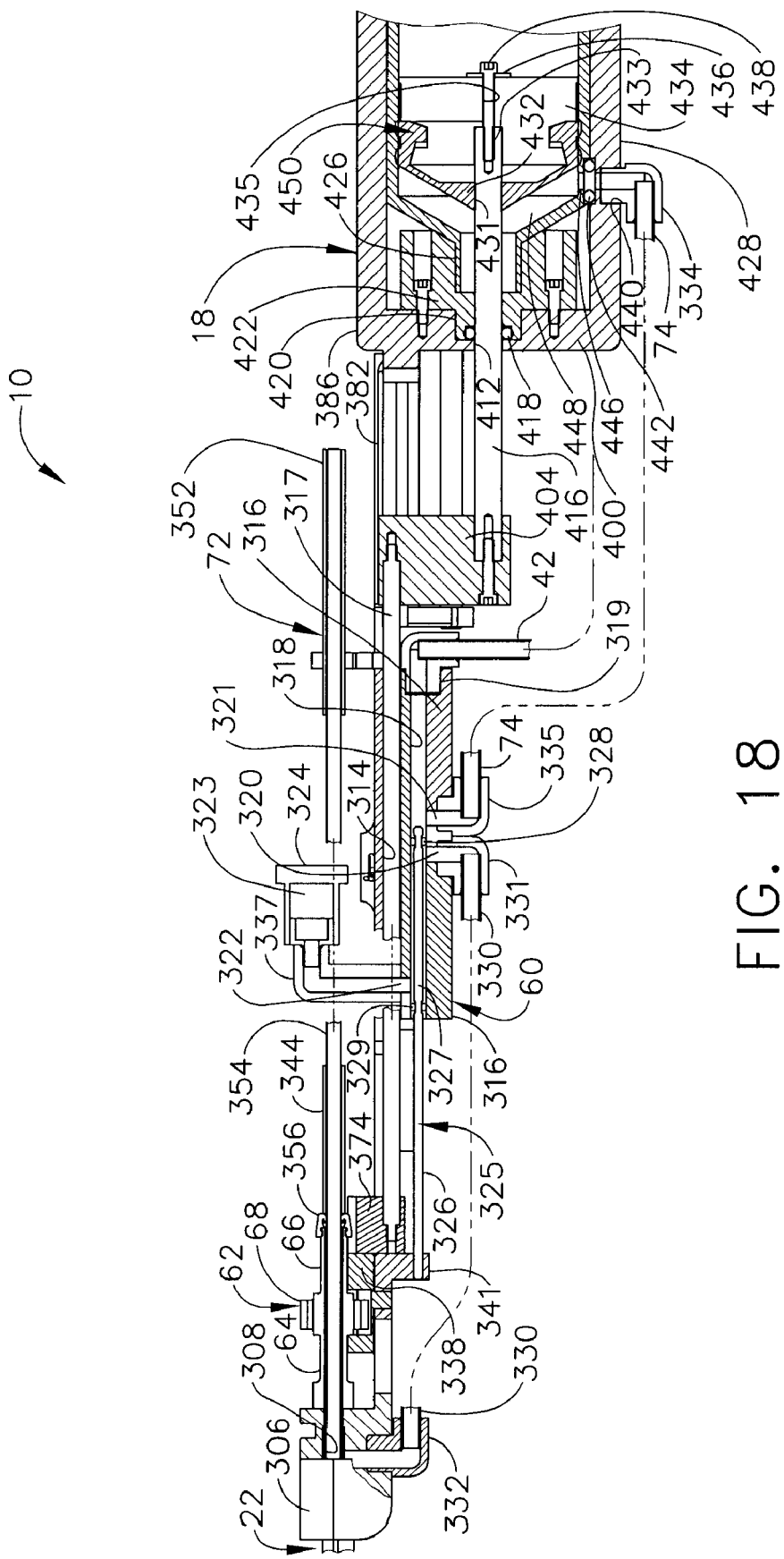
FIG. 18 is a left side section view of the disposable probe assembly of FIG. 1 taken generally through a longitudinal axis and omitting a probe cannula.

With particular reference to FIGS. 15, 18, a distal portion of the upwardly open longitudinal trough 310 is also downwardly open. A distally and proximally open, longitudinally aligned valve bore 318 is formed in a lower portion of the proximal block portion 316. A proximal 90 degree fitting 319 seals a proximal opening of the valve bore 318 to an upper end of the external conduit 42. Central and proximal ports 320, 321 communicate with the valve bore 318 laterally from a left side of the proximal block portion 316 and a distal port 322 communicates laterally from a left side of the proximal block portion 316. A right distal 90-degree fitting 337 communicates between the distal port 322 and an intake filter 323 within an outer hose fitting 324.

A valve control rod 325 has a distal actuating portion 326 extending distally out of the valve bore 318 with a distal end positionable under the downwardly open portion of the longitudinal trough 310. The valve control rod 325 also has a valve spool portion 327 that longitudinally translates within the valve bore 318 to selectively position between a first position and a second position. A proximal O-ring 328 near a proximal end of the valve spool portion 327 and a distal O-ring 329 are spaced such that the first position entails the O-rings 328, 329 bracketing the central and distal ports 320, 322 and the second position entails the O-rings 328, 329 bracketing the proximal and central ports 321, 320, respectively.

Figure 17:
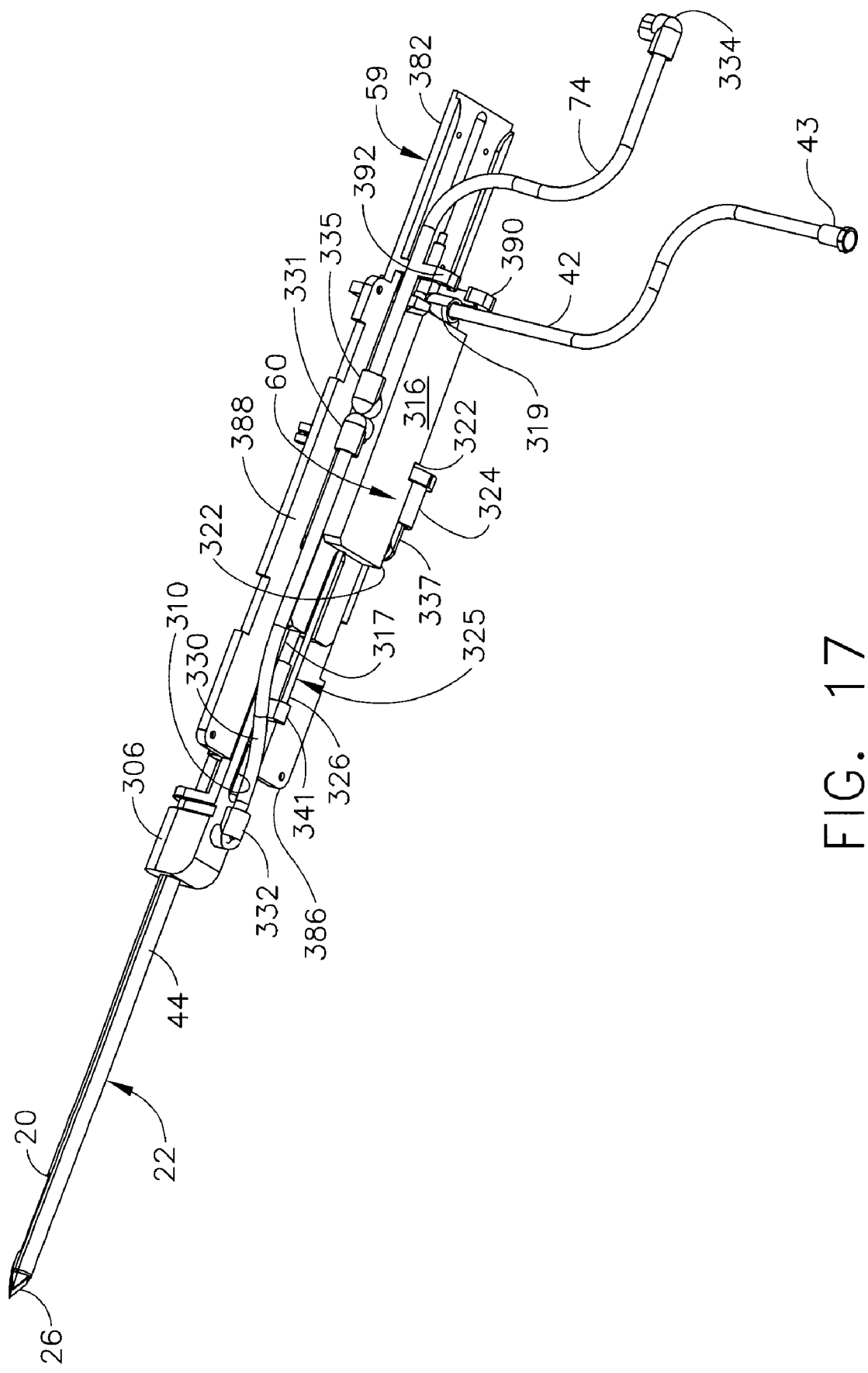
FIG. 17 is a bottom left isometric view of the distal internal portion of the disposable probe assembly of FIG. 1 with the bottom cover removed.

In FIGS. 17-18, the distal vacuum conduit 330 has one end attached to a center ninety-degree fitting 331 attached to the central port 320 and the other end attached to a probe union ninety-degree fitting 332 that communicates with the lateral lumen 44. The vacuum source conduit 74 has one end attached to a canister ninety degree fitting 334 and the other attached to a proximal ninety degree fitting 335 attached to the proximal port 321.

In FIGS. 15, 18, the front actuation finger 206 of the front carriage 134 (FIG. 9) is received within an upwardly open socket 336 formed on a left side of a vacuum control shuttle 338 having a lateral concave recessed band 340 shaped to encompass with a clearance a lower portion of the rotation spur gear section 68 of the cutter gear 62. The vacuum control shuttle 338 is laterally sized to bridge the longitudinally open trough 310 with an L-shaped connector 341 attached to an undersurface of the vacuum control shuttle 338 sized to reside within the longitudinal trough 310 and to extend its vertical and proximal portion below the longitudinal trough 310 to attach to the distal end of the vacuum actuating portion 326 of the valve control rod 325.

A straw holder 342 of the straw assembly 72 includes a distal sleeve 344 with a leftward projection 346 near its distal end and attached at its proximal left edge to an elongate splint member 348 having a midpoint indented feature 350 and attached along its proximal rightward surface to a proximal sleeve 352. A straw 354 is received through the proximal sleeve 352, to the right of the elongate splint member 348, through the distal sleeve 344, and on through a rear dynamic seal 356 attached to a proximal end of the cutter gear 62, and into the cutter tube 36. A support plate 358 traversely fastened to an aft surface of the probe support body 60 has a downwardly open notch 360 that allows connection of the proximal 90 degree fitting 319 and passage of the distal vacuum pump rod 317. An upper guide hole 362 receives the proximal sleeve 352 of the straw holder 342.

A straw hook wire 364 keeps the straw assembly 72 in place upon the probe support body 60 prior to engagement with the reusable handpiece 12. A curled lower right end passes into leftwardly opening 365 along the top right surface of the proximal block portion 316 of the probe support body 60 into a small mounting block 366 extending upwardly from a right side with a downwardly inserted pin 368 passing through the curled lower right end to hold the straw hook wire 364 in place. The straw hook wire 364 has a horizontal portion attached to the curled end that passes under the straw 354 and elongate splint member 348, bending upward within the midpoint indented feature 350 and then bending leftward and horizontally again through a lateral slot 370 in a vertical wire support member 372 formed onto a left side of the top surface of the proximal block. portion 316. It should be appreciated that engagement of the reusable handpiece 12 forces the left portions of the straw hook wire 364 out of engagement with the midpoint indented feature 350 as a rib feature 373 (FIG. 9) deflects the left portion of the straw hook wire 364. Thus, translation of the aft carriage 136 may cause translation of the straw assembly 72.

With further reference to FIG. 15, proximal to the vacuum control shuttle 338, a vacuum pump shuttle 374 is also laterally sized to bridge the longitudinal trough 310 with an integral lower central portion sized to reside within the longitudinal trough 310 and to attach to a distal end of the vacuum pump rod 317. A backward projecting locking arm 376 attached to a left side of the vacuum pump shuttle 374 has an inward proximal hook 378 that is resiliently inwardly biased. The top extension member 59 has an aft horizontal surface 382 sized to overlay a distal canister support structure 384 (FIG. 16) attached to an upper canister portion 386 (FIG. 16) of the vacuum syringe assembly 18. The top extension member 59 also has a right horizontal surface 386 and a left horizontal surface 388 extending forward from the distal corners of the aft horizontal surface 382 that surround the top surface of the probe support body 60 covering the gap to the top edges of the bottom cover 48. Right and left legs 390, 392 extend downward with inwardly curled edges at the juncture respectively between the right horizontal surface 386 and aft horizontal surface 382 and the juncture between the left horizontal surface 388 and the aft horizontal surface 382. Along an inner surface of the left horizontal surface 388, a kick-out ridge 394 extends upwardly, longitudinally positioned to coincide with full distal travel of the vacuum pump shuttle 374, which coincides with an initial condition of the disposable probe assembly 14 with the straw assembly 72 locked forward by the straw hook wire 364 and the side aperture 20 of the probe cannula 22 closed by the cutter tube 36.

Figure 16:
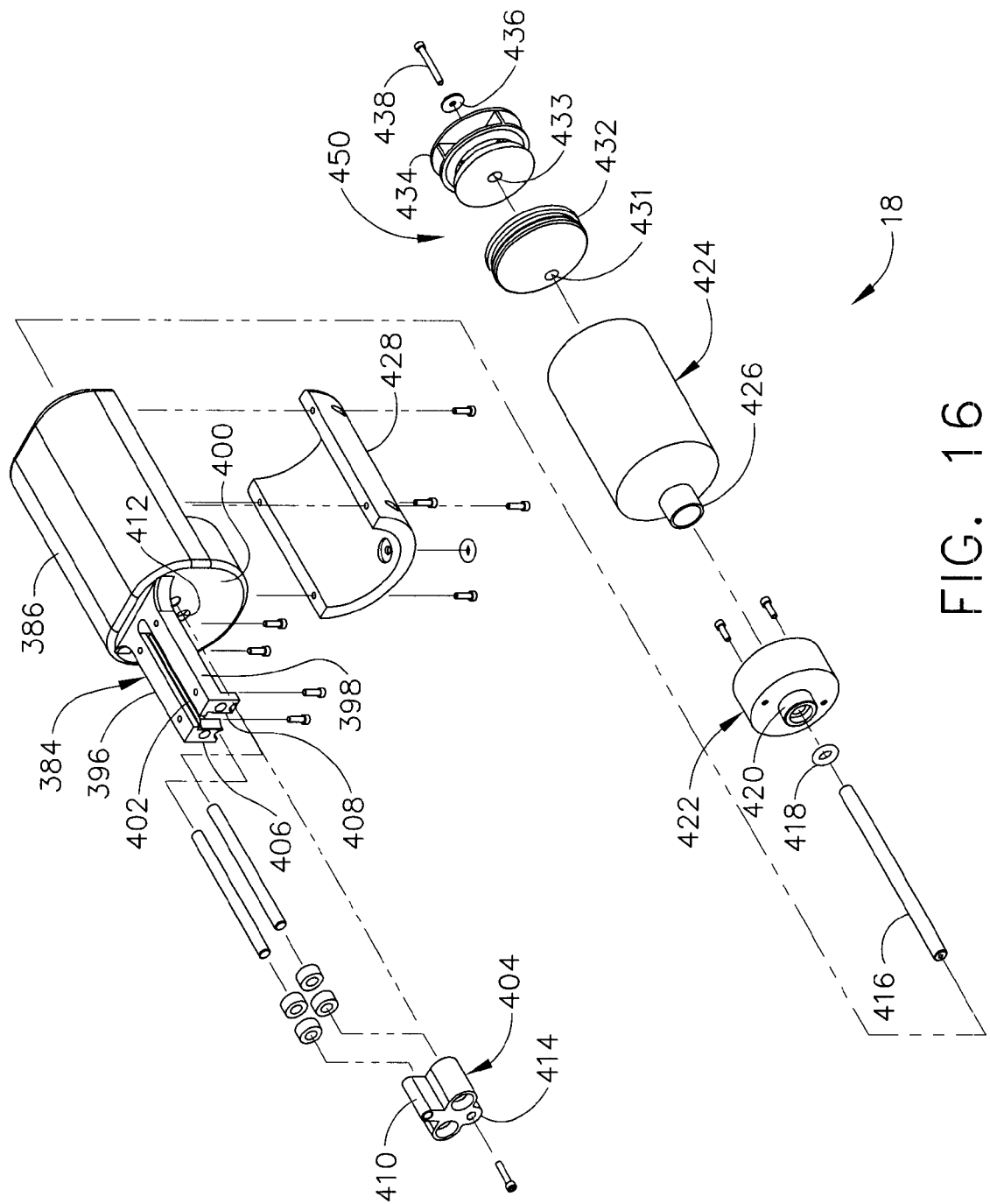
FIG. 16 is a left front exploded view of a proximal portion (vacuum syringe assembly) of the disposable probe assembly of FIG. 1.

With particular reference to FIG. 16, the vacuum syringe assembly 18 is configured to respond to longitudinal translation of the distal vacuum pump rod 317. In particular, the canister support structure 384 includes a right rail bracket 396 and a left rail bracket 398, joined at their proximal ends to one another and to an upper portion of a distal circular face 400 of the upper canister portion 386 with a distally and vertically open longitudinal guide slot 402 defined between the rail brackets 396, 398. A connection block 404 with a transverse cross section similar to a cloverleaf with a narrowed upper lobe translates between the distal circular face 400 and right and left down-turned mounting surfaces 406, 408 of the right and left rail brackets 396, 398 respectively that are attached to the aft surface of the probe support body 60.

An upper narrowed projection 410 of the connection block 404 is fastened to a proximal end of the distal vacuum pump rod 317 (FIG. 18) and shaped to slide within the guide slot 402. A hole 412 centered on the distal circular face 400 is aligned with a small lower protuberance 414 of the connection block 404. A proximal vacuum pump rod 416 is attached to a proximal side of the small lower protuberance 414 and passes through the hole 412 and on through a dynamic O-ring seal 418 within a neck 420 of a seal cup 422 that is fastened to the proximal side of the distal circular face 400 of the upper canister portion 386. The proximal end of the proximal vacuum pump rod 416 passes on through a vacuum pump cylinder 424 whose bottle neck 426 and distal portion fits within the seal cup 422. Lateral sides of the vacuum pump cylinder 424 are closely encompassed by fastening together the upper container portion 386 to a lower canister portion 428 with a proximal circular opening closed by a canister end cap. 430 (FIG. 2).

With particular reference to FIGS. 16 and 18, a proximal end of the proximal vacuum pump rod 416 passes through a central hole 431 in a tension plunger seal 432, partially through an enlarged distal central hole 433 in a tension plunger body 434 that proximally communicates with a smaller proximal central hole 435 too small for the proximal vacuum pump rod 416. A washer 436, centered on a proximal face of the tension plunger body 434, is held on by a small bolt 438 that passes distally into the smaller proximal central hole 435 and is threaded into the proximal vacuum pump rod 416. The canister ninety-degree fitting 334 passes through a bottom hole 440 in the lower canister portion 428. With particular reference to FIG. 18, an O-ring 442 between the lower canister portion 428 and the vacuum pump cylinder 424 form a static seal between the bottom hole 440 and an aligned distal bottom hole 446 to communicate with a variable volume vacuum cavity 448 whose volume is dictated by the longitudinal position of a syringe plunger assembly 450 formed by the combination of the tension plunger seal and body 432, 434.

Figure 19:
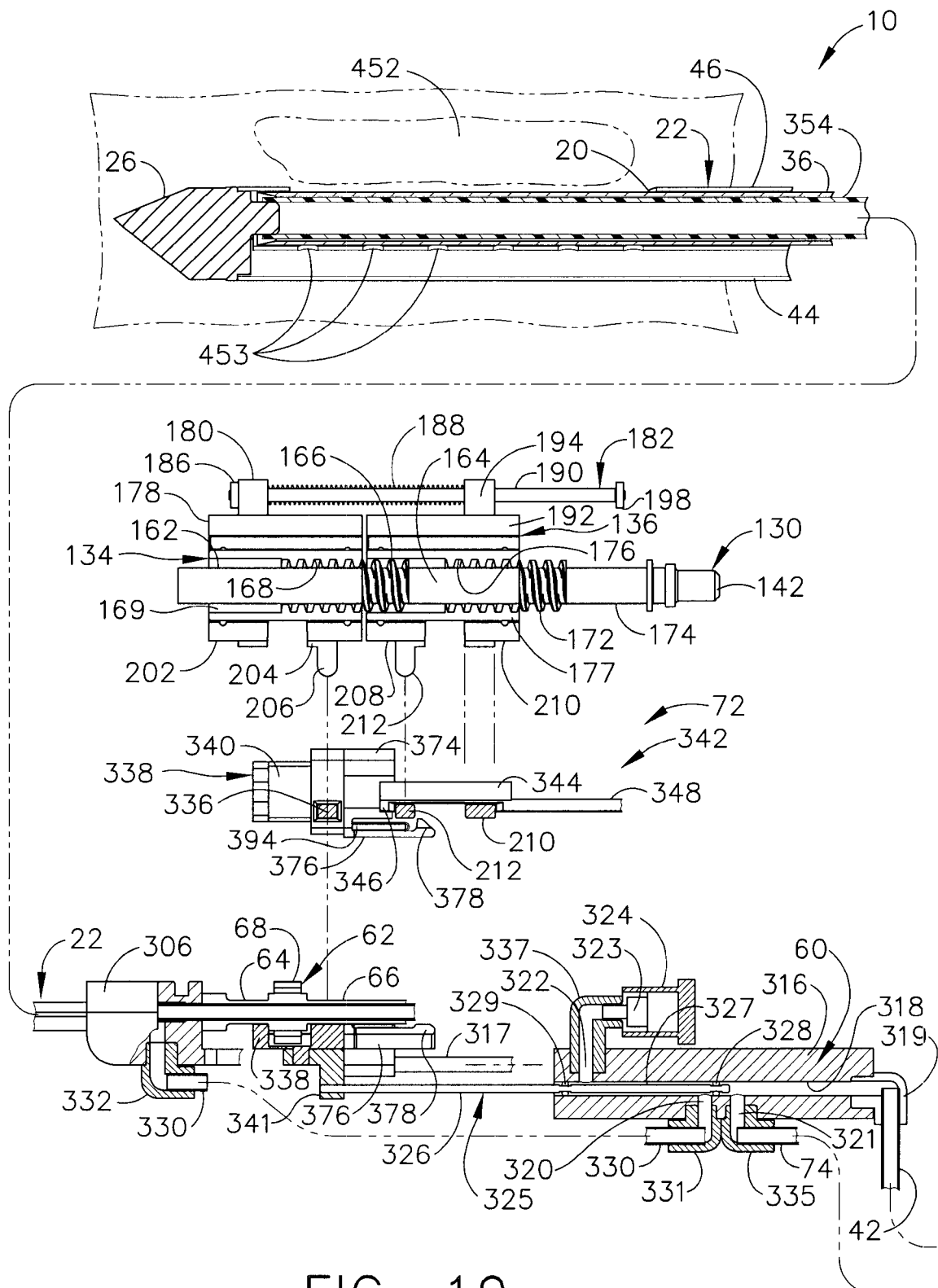
FIG. 19 is a left side diagrammatic view of an initial state of the biopsy device of FIG. 1 with the vacuum syringe assembly omitted and with both carriages distally positioned and engaged to the disposable probe assembly.

In use, in FIG. 18, the disposable biopsy assembly 14 is in an initial condition with the cutter gear 62 distally positioned, which closes the side aperture 20 in the probe cannula 22 for insertion (FIG. 19). In addition, the underlying vacuum control shuttle 338 is at its distal position, moving the valve control rod 325 distally to the first position with the atmospheric air made available through the distal port 322 to the central port 320 to the lateral lumen 44 of the probe cannula 22. The vacuum pump shuttle 374 is distally positioned behind the vacuum control shuttle 338 in its most distal position drawing distally the distal vacuum pump rod 317, connection block 404, proximal vacuum pump rod 416, and finally the vacuum syringe plunger 450 to an unactuated state. In addition, the straw assembly 72 is also distally advanced with the straw 354 inserted through the cutter tube 36.

In FIG. 19, the reusable handpiece 12 is mounted onto the disposable probe assembly 14 in the same state as FIG. 18. The front (cutter) carriage 134 of the reusable handpiece 12 engages the cutter gear 62 for longitudinal movement, as well as extending downwardly projecting front actuation finger 206 into engagement with the upwardly open socket 336 of the vacuum control shuttle 338. The aft (straw) carriage 136 of the reusable handpiece 12 engages the straw assembly 72 for longitudinal movement, as presenting the downwardly projecting aft actuation finger 212 to leftward projection 346 of the straw assembly 72. With the biopsy device 10 thus prepared, the piercing tip 26 is inserted into tissue with the side aperture 20 placed beside a suspicious lesion 452.

Figure 20:
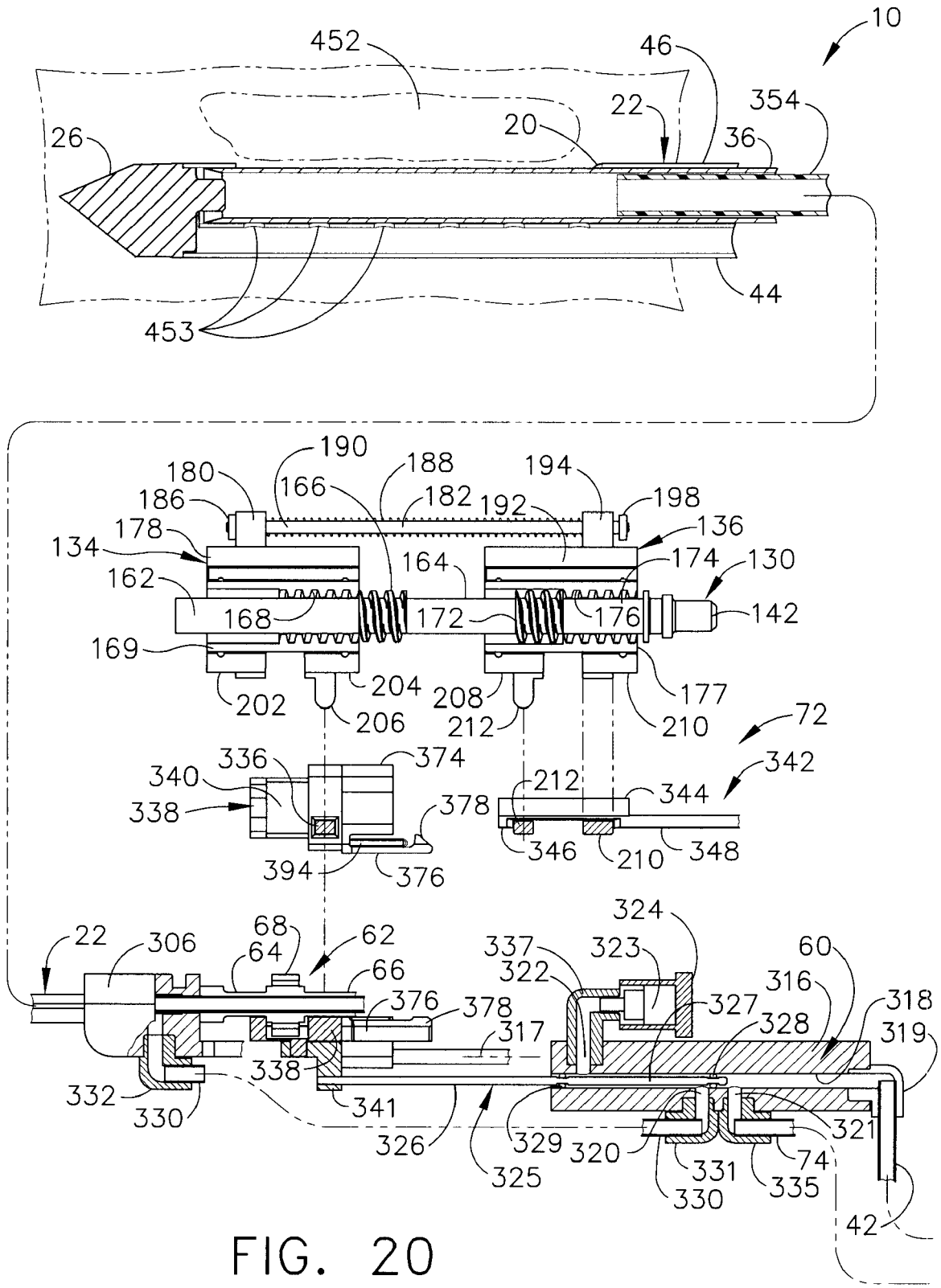
FIG. 20 is a left side diagrammatic view of the biopsy device of FIG. 1 with the vacuum syringe assembly omitted, depicted after insertion of the probe cannula into tissue and the retraction of an aft (straw) carriage that withdraws a straw from the cutter tube.

In FIG. 20, the reusable handpiece 12 prepares the disposable probe assembly 14 by rotating the translation shaft 130 in the direction that retracts the aft carriage 136 whose threaded bore 176 is engaged to the aft threaded portion 172 while the front carriage 134 free wheels on the distal overrun portion 162, which causes the straw 354 to retract within the cutter tube 36. As the aft carriage 136 approaches its proximal most position, the aft carriage 136 reaches the full travel of the carriage limiting rod 182, which thus pulls the threaded bore 168 of the front carriage 134 onto the front threaded portion 166, overcoming the bias of the long compression spring 188 on the carriage limiting rod 182.

Figure 21:
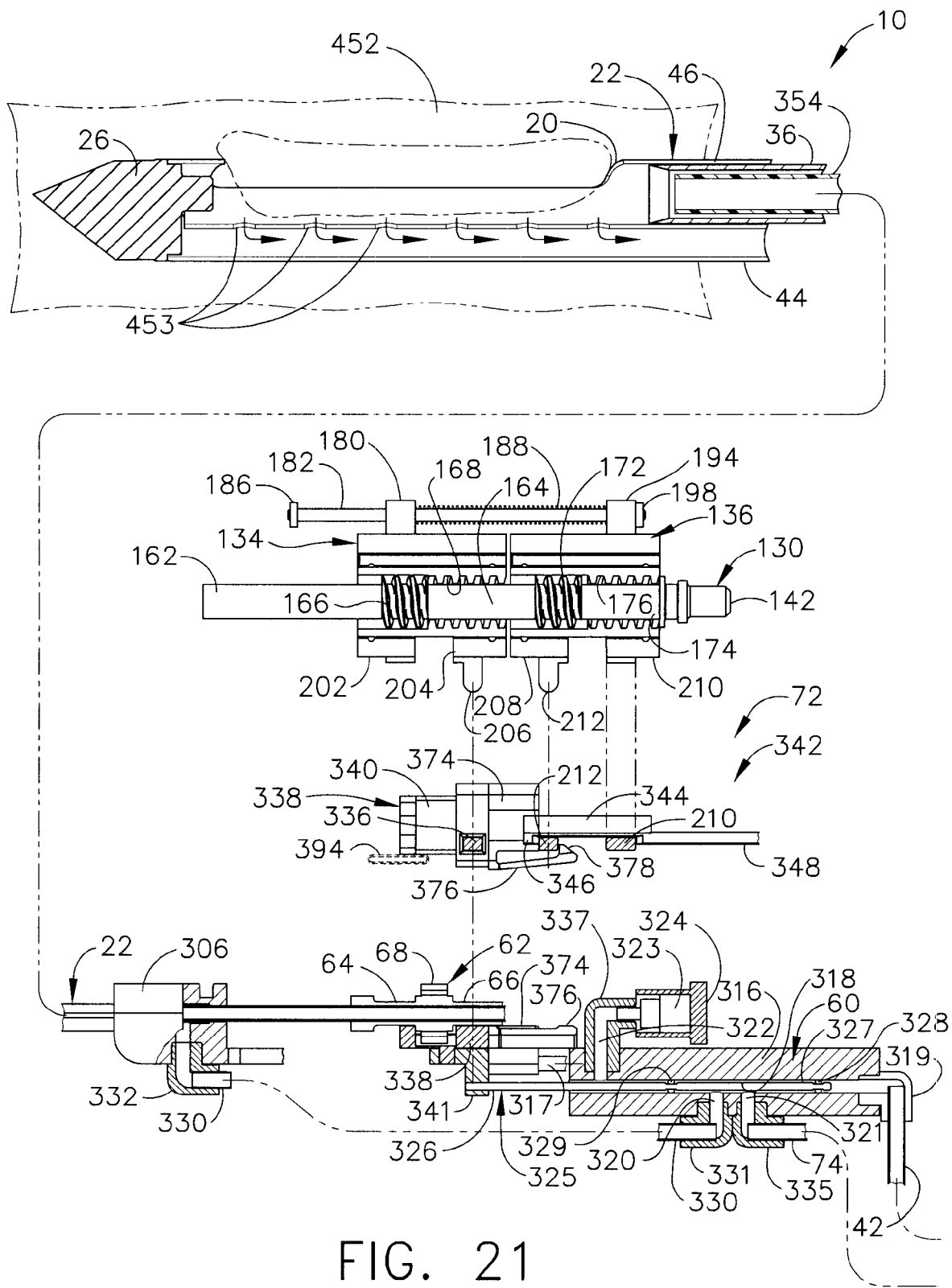
FIG. 21 is a left side diagrammatic view of the biopsy device of FIG. 1 with the vacuum syringe assembly omitted, depicted after retraction of a front (cutter) carriage that positions a valve and retracts a vacuum plunger to perform vacuum assistance within the probe cannula.

In FIG. 21, continued rotation of the translation shaft 130 with the aft carriage 136 free wheeling on the proximal overrun portion 174 causes the front carriage 134 to retract to the center overrun portion 164 and freewheel, while proximally moving the vacuum control shuttle 338 and thus moving the vacuum control rod 325 proximally to the second position with the lateral lumen 44 communicating through the central port 320 to the proximal port 321 to the variable volume vacuum cavity 448 of the vacuum syringe assembly 18 which increases in volume as the vacuum pump shuttle 374 is driven aft by the vacuum control shuttle 338. A sample indicator (not shown) located within the straw assembly 72 closes the lumen within the straw 354, resulting in a low pressure ("vacuum") as compared to atmospheric pressure within the lateral lumen 44. This low pressure is presented to the side aperture 20 as the cutter tube 36 retracts, passing through internal holes 453 passing between the lateral and cutter lumens 44, 46 beneath the side aperture 20, prolapsing a portion of the suspicious lesion 452 into the cutter lumen 46. The backward projecting locking arm 376 of the vacuum pump shuttle 374 engages the downwardly projecting aft actuation finger 212 of the aft carriage 136.

Figure 22:
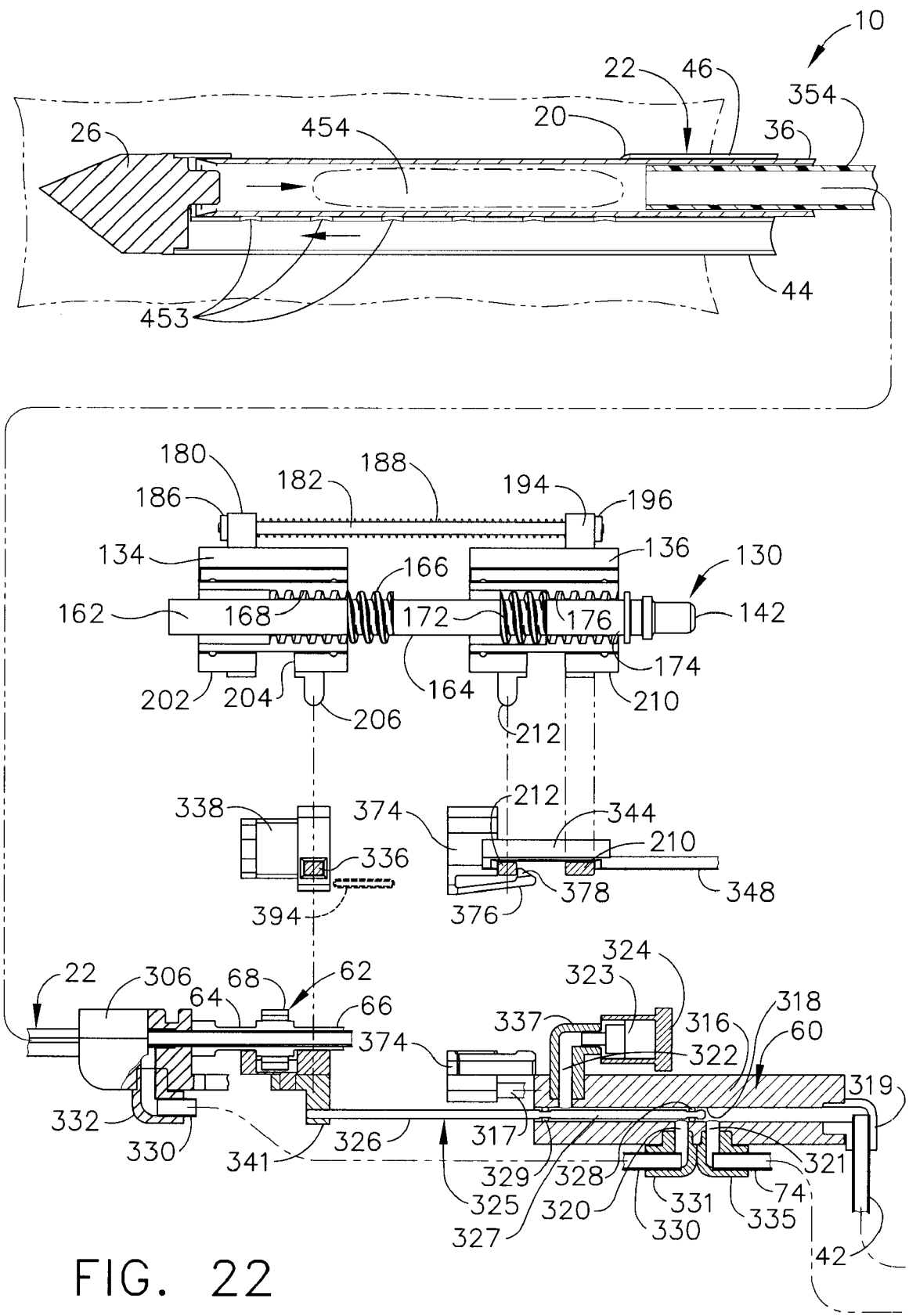
FIG. 22 is a left side diagrammatic view of the biopsy device of FIG. 1 with the vacuum syringe assembly omitted, depicted after distal advancement of the front (cutter carriage) as the aft (straw) carriage begins to distally translate to insert the straw over a severed tissue sample and to reset the vacuum syringe assembly.

In FIG. 22, with the vacuum pump shuttle 374 thus held to keep vacuum assistance available, the front carriage 134 is distally translated by rotation of the translation shaft 130 in the opposite direction. In particular, the long compression spring 188 on the carriage limiting rod 182 urges the threaded bore 168 of the front carriage 134 into engagement with the front threaded portion 166 while the bias from the long compression spring 188 also biases the aft carriage 136 to remain free wheeling on the proximal overrun portion 174. Although not shown in FIG. 22, it should be appreciated that the rotation shaft 128 is rotating the cutter gear 62 and thus the cutter tube 36 in a ratio related to the rate of translation. When the front carriage 134 reaches full distal travel, the vacuum control shuttle 338 switches the vacuum control rod 325 to the first position that vents the lateral lumen 44 to the atmosphere while the straw assembly 72 maintains a residual vacuum behind a severed tissue sample 454 in the cutter lumen 46. The differential pressure on the sample 454 assists in retracting the sample 454. In particular, as the carriage limiting rod 182 reaches full separation between the carriages 134, 136, the aft carriage 136 is drawn onto the aft threaded portion 172 to distally translate both the vacuum pump shuttle 374 and the straw assembly 72 so that the straw 354 encompasses the severed tissue sample 454 with the biopsy device 10 returned to the position of FIG. 19. Operation as described for FIG. 20 retracts the sample 454 preparing the device for repositioning as desired and the taking of another core biopsy sample.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

While preferred embodiments of the present invention have been shown and described herein, it will be obvious to those skilled in the art, given the benefit of the present disclosure, that such embodiments are provided by way of example only. Numerous variations, changes, and substitutions will now occur to those skilled in the art without departing from the spirit and scope of the appended claims.

While advantageous sequencing allows vacuum to be stored and used in relation to two carriages, applications consistent with the present invention may include other operable coupling of a motor contained in a hand-held proximal portion of a biopsy device, such as coupling the motor to turn a vacuum pump that evacuates a fixed volume vacuum accumulator. As another example, the motor may wind up a reel that positions a plunger of a vacuum syringe.

As another example, for imaging modalities such as magnetic resonance imaging (MRI), the power supplies, control circuitry and motor may be selected from technologies that are inherently immune to a strong magnetic field and/or shielded to avoid transmission of radio frequency (RF) interference that may create artifacts in the diagnostic images. Alternatively or in addition, certain components may be remote to the hand-held device such as the DC motor connected by a mechanical drive cable.

As yet another example, instead of segregating the vacuum syringe assembly to the disposable probe assembly, a vacuum container that is evacuated or otherwise causes to contain a low pressure by a motor-driven mechanism may be part of a reusable handpiece pneumatic conduits that communicate to a probe assembly.

What is claimed:

1. A biopsy device, comprising:
   a probe cannula defining an internal passage;
   a proximal portion attached to the probe cannula positionable to insert the probe cannula into tissue;
   a cutter reciprocally received by the probe cannula to sever a tissue sample received in the probe cannula;
   a pneumatic container attached with the proximal portion and operably configured to communicate a low pneumatic pressure contained within the pneumatic container with the probe cannula;
   a motor contained in the proximal portion operatively coupled to translate the cutter, wherein the motor is further operatively coupled to reduce pneumatic pressure in the pneumatic container; and
   a frame assembly positioned within the biopsy device adjacent the proximal portion and attached to the probe cannula, wherein the frame assembly is longitudinally movable within the biopsy device, wherein the motor is further operably configured to impart a longitudinal reciprocating motion to the frame assembly during insertion of the probe cannula into tissue.

2. The biopsy device of claim 1, wherein the pneumatic container comprises a vacuum syringe comprising a vacuum cylinder and a plunger, the motor operatively coupled to the plunger.

3. The biopsy device of claim 1, wherein the probe cannula comprises a cylindrical probe tube having a side aperture sized to admit prolapsed tissue, the cutter comprising a cutter tube axially offset within the probe tube to closely reciprocate past the side aperture.

4. The biopsy device of claim 1, wherein the probe cannula comprises a cutter lumen having a side aperture, the cutter comprising a cutter tube sized to reciprocate within the cutter lumen, further comprising a lateral lumen distally communicating with the side aperture and defining the internal passage.

5. The biopsy device of claim 1, further comprising a straw assembly positioned proximal to the cutter tube, the motor further operatively configured to longitudinally translate the straw assembly through the cutter tube to retract a severed tissue sample.

6. The biopsy device of claim 5, further comprising a straw carriage received on a translation shaft coupled to the straw assembly.

7. The biopsy device of claim 1, further comprising a cutter carriage received on a translation shaft coupled to the cutter.

8. The biopsy device of claim 7, wherein the pneumatic container comprises a vacuum cylinder and plunger, the biopsy device further comprising a vacuum pump shuttle retracted by movement of the cutter carriage to position the plunger in the vacuum cylinder to create a low pressure.

9. The biopsy device of claim 7, further comprising a vacuum assistance valve operably switched by the cutter carriage to communicate a low pressure from the pneumatic container to the probe cannula.

10. The biopsy device of claim 1, further comprising a handpiece cover containing a motor driven carriage assembly and comprising a probe assembly, the probe assembly further comprising a cover engageable to the handpiece cover and attached to the probe cannula, the pneumatic container attached to a selected one of the handpiece cover and the probe assembly cover.

11. The biopsy device of claim 1, wherein the probe cannula comprises a cylindrical probe tube having a side aperture sized to admit prolapsed tissue, the cutter comprising a cutter tube axially offset within the probe tube to closely reciprocate past the side aperture.

12. The biopsy device of claim 1, wherein the probe cannula comprises a cutter lumen having a side aperture, the cutter comprising a cutter tube sized to translate within the cutter lumen, further comprising a lateral lumen distally communicating with the side aperture and defining the internal passage.

13. The biopsy device of claim 1, further comprising a motor driven carriage assembly and a straw assembly positioned proximal to the cutter, the motor driven carriage assembly further operatively configured to longitudinally translate the straw assembly through the cutter to retract a severed tissue sample.

14. The biopsy device of claim 13, further comprising a translation shaft rotated by the motor, and a straw carriage received on the translation shaft coupled to the straw assembly.

15. The biopsy device of claim 1, further comprising a motor driven carriage assembly and a translation shaft rotated by the motor, wherein a cutter carriage is received on the translation shaft coupled to the cutter.

16. The biopsy device of claim 15, wherein the pneumatic container comprises a vacuum syringe comprising a vacuum cylinder and a plunger, wherein the biopsy device further comprises a vacuum pump shuttle retracted by movement of the cutter carriage to position the plunger in the vacuum cylinder to create a low pressure.

* * * * *